(12) United States Patent
Weiner et al.

(10) Patent No.: US 9,072,562 B2
(45) Date of Patent: Jul. 7, 2015

(54) BONE JOINING DEVICE, KIT AND METHOD

(71) Applicant: Nextremity Solutions, LLC, Colts Neck, NJ (US)

(72) Inventors: Lon S. Weiner, Rumson, NJ (US); Stuart D. Katchis, Scarsdale, NY (US); Arthur A. Alfaro, Colts Neck, NJ (US); Willem H. P. Van Iperen, Westfield, NJ (US); Mari S. Truman, Warsaw, IN (US)

(73) Assignee: Nextremity Solutions, Inc., Red Bank, NJ (US)

( * ) Notice: Subject to any disclaimer, the term of this patent is extended or adjusted under 35 U.S.C. 154(b) by 259 days.

(21) Appl. No.: 13/646,146

(22) Filed: Oct. 5, 2012

(65) Prior Publication Data

US 2013/0274814 A1    Oct. 17, 2013

Related U.S. Application Data

(63) Continuation-in-part of application No. 12/709,426, filed on Feb. 19, 2010, now Pat. No. 8,715,325.

(60) Provisional application No. 61/153,907, filed on Feb. 19, 2009.

(51) Int. Cl.
*A61B 17/86* (2006.01)
*A61B 17/88* (2006.01)
(Continued)

(52) U.S. Cl.
CPC ......... *A61B 17/8685* (2013.01); *A61B 17/8875* (2013.01); *A61B 17/86* (2013.01); *A61F 2/4225* (2013.01); *A61B 17/1682* (2013.01); *A61F 2/4606* (2013.01); *A61B 17/7291* (2013.01); *A61F 2002/30331* (2013.01);
(Continued)

(58) Field of Classification Search
CPC ............... A61B 17/86; A61B 17/8685; A61B 17/7291; A61B 17/8875; A61B 17/8883
USPC ................................ 606/86 R, 104, 246–299
See application file for complete search history.

(56) References Cited

U.S. PATENT DOCUMENTS 3,991,425 A    11/1976   Martin et al.
4,246,662 A    1/1981    Pastrick
(Continued)

FOREIGN PATENT DOCUMENTS

DE    19949890 A1    6/2001
EP    0831757 B1     11/2001
(Continued)

OTHER PUBLICATIONS

Caterini, et al., "Arthrodesis of the Toe Joints with an INtramedullary Cannulated Screw for Correction of Hammertoe Deformity," Foot & Ankle International, 2004, pp. 256-261, vol. 25, No. 4.
(Continued)

*Primary Examiner* — Christopher Beccia
(74) *Attorney, Agent, or Firm* — Heslin Rothenberg Farley & Mesiti P.C.

(57) ABSTRACT

Provided is a bone joining device suitable for joining a first bone piece to a second bone piece. Also provided is a method of joining a first bone piece with a second bone piece in a living mammal. The method comprises inserting the above bone joining device between the first bone piece and the second bone piece.

34 Claims, 33 Drawing Sheets

(51) Int. Cl.
*A61B 17/16* (2006.01)
*A61B 17/72* (2006.01)
*A61F 2/42* (2006.01)
*A61F 2/46* (2006.01)
*A61F 2/30* (2006.01)

(52) U.S. Cl.
CPC ............... *A61F 2002/30481* (2013.01); *A61F 2002/30487* (2013.01); *A61F 2002/30497* (2013.01); *A61F 2002/30551* (2013.01); *A61F 2002/3085* (2013.01); *A61F 2002/423* (2013.01); *A61F 2002/4235* (2013.01); *A61B 17/8883* (2013.01); *A61B 17/862* (2013.01); *A61B 17/8888* (2013.01)

(56) References Cited

U.S. PATENT DOCUMENTS

| | | |
|---|---|---|
| 4,304,011 A | 12/1981 | Whelan, III |
| D277,784 S | 2/1985 | Sgarlato et al. |
| 4,908,031 A | 3/1990 | Frisch |
| 5,037,440 A | 8/1991 | Koenig |
| 5,047,059 A * | 9/1991 | Saffar ............... 623/21.15 |
| 5,062,851 A | 11/1991 | Branemark |
| 5,129,903 A | 7/1992 | Luhr et al. |
| 5,167,661 A | 12/1992 | Wagenknecht |
| 5,207,712 A | 5/1993 | Cohen |
| 5,290,314 A | 3/1994 | Koch et al. |
| 5,417,692 A * | 5/1995 | Goble et al. ............... 606/311 |
| 5,443,467 A | 8/1995 | Biedermann et al. |
| 5,683,466 A | 11/1997 | Vitale |
| 5,725,581 A | 3/1998 | Branemark |
| 5,810,591 A | 9/1998 | Huber |
| 5,810,822 A | 9/1998 | Mortier |
| 5,827,285 A | 10/1998 | Bramlet |
| 5,919,193 A | 7/1999 | Slavitt |
| 6,099,571 A | 8/2000 | Knapp |
| 6,284,001 B1 | 9/2001 | Knapp |
| 6,383,223 B1 | 5/2002 | Baehler et al. |
| 6,413,260 B1 | 7/2002 | Berrevoets et al. |
| 6,454,808 B1 | 9/2002 | Masada |
| 6,458,134 B1 * | 10/2002 | Songer et al. ............... 606/304 |
| 6,517,543 B1 | 2/2003 | Berrevoets et al. |
| 6,602,293 B1 | 8/2003 | Biermann et al. |
| 6,852,113 B2 | 2/2005 | Nathanson et al. |
| 6,964,994 B1 | 11/2005 | Antonietti et al. |
| 7,041,106 B1 | 5/2006 | Carver et al. |
| 7,214,226 B2 | 5/2007 | Alleyne |
| 7,291,175 B1 | 11/2007 | Gordon |
| 7,297,165 B1 | 11/2007 | Kriek |
| 7,611,526 B2 | 11/2009 | Carl et al. |
| 7,635,364 B2 | 12/2009 | Barrall et al. |
| 7,837,738 B2 | 11/2010 | Reigstad et al. |
| 8,100,983 B2 | 1/2012 | Schulte |
| 8,303,589 B2 | 11/2012 | Tyber |
| 8,313,487 B2 | 11/2012 | Tyber |
| 8,328,806 B2 | 12/2012 | Tyber |
| 2004/0127900 A1 | 7/2004 | Konieczynski et al. |
| 2004/0220678 A1 | 11/2004 | Chow et al. |
| 2005/0043732 A1 | 2/2005 | Dalton |
| 2005/0113830 A1 | 5/2005 | Rezach et al. |
| 2005/0192587 A1 | 9/2005 | Lim |
| 2006/0052878 A1 | 3/2006 | Schmieding |
| 2006/0074492 A1 | 4/2006 | Frey |
| 2006/0195087 A1 | 8/2006 | Sacher et al. |
| 2008/0045963 A1 | 2/2008 | Abdou |
| 2008/0065224 A1 | 3/2008 | Reigstad et al. |
| 2008/0097611 A1 | 4/2008 | Mastrorio et al. |
| 2009/0157121 A1 | 6/2009 | Harris et al. |
| 2010/0036439 A1 | 2/2010 | Lavi |
| 2010/0121325 A1 | 5/2010 | Tyber |
| 2010/0256638 A1 | 10/2010 | Tyber |
| 2011/0054545 A1 | 3/2011 | Champagne |
| 2011/0082508 A1 | 4/2011 | Reed |
| 2011/0118739 A1 | 5/2011 | Tyber |
| 2011/0125153 A1 | 5/2011 | Tyber |

FOREIGN PATENT DOCUMENTS

| | | |
|---|---|---|
| GB | 1582974 A | 1/1981 |
| GB | 2126097 A | 3/1984 |
| JP | 2005073740 A | 3/2005 |
| WO | 9309728 A1 | 5/1992 |
| WO | 9605784 A1 | 2/1996 |
| WO | 9716137 A1 | 5/1997 |
| WO | 2007109752 A2 | 9/2007 |

OTHER PUBLICATIONS

DE 19949890, Published Jun. 7, 2001, abstract only in English, downloaded from espacenet.com, 2 pages.

Edwards and Beischer, "Interphalangeal Join Arthrodesis of the Lesser Toes," Foot & Ankle Clinics North America, 2002, pp. 43-48, vol. 7.

Hetherington, "Metatarsalgia and Lesser Metatarsal Surgery," Hallux Valgus and Forefront Surgery textbook, 2000, pp. 429-451.

International Serch Report dated Jul. 9, 2010 in related PCT Appln. No. PCT/US10/024833, filed Feb. 19, 2010.

Iselin, et al. "Desarthodesis-Arthroplasties Interphalangiennes Proximales-" Conversion to Arthroplasty from Proximal Interphalangeal Joint Arthrodesis, Annales de Chirurgie de la Main, 1988, pp. 115-119, vol. 7, No. 2.

JP 2005073740, PUblished Mar. 24, 2005, abstract only in English, downloaded from espacenet.com, 1 page.

Konkel, et al., "Hammer Toe Correction Using an Absorbable Intramedullary Pin," Foot & Ankle International, 2007, pp. 916-920, vol. 28, No. 8.

Murray, "Surface Replacement Arthoplasty of the Proximal Interphalangeal Joint," The Journal of Hand Surgery, 2007, pp. 899-904, vol. 32A. No. 6.

SHIP Implant Brochure, Sgarlato Hammertoe Implant Procedure, Sgarlato Labs, Campbell, CA, 2006, 2 pages.

Sokolow, "une prothese de l'articulation interphlangienne prximale osteo-integree: IPP 2. Premier Resultsant—Short Term Results of the IPP 2 Proximal Interphalangeal Joint Prosthesis," Chirgurgi de la Main, 2006, pp. 280-285, vol. 25, abstract only in English.

* cited by examiner

BONE JOINING DEVICE, KIT AND METHOD

CROSS-REFERENCE TO RELATED APPLICATIONS

The present application is a continuation-in-part of U.S. Nonprovisional application Ser. No. 12/709,426 filed 19 Feb. 2010, which claims the benefit of U.S. Provisional Application Ser. No. 61/153,907 filed 19 Feb. 2009; which are incorporated herein by reference in their entireties.

FIELD OF THE INVENTION

This application relates to devices and methods for joining bones.

BACKGROUND

Hammertoe deformity, the most common deformity of the lesser toes, is a flexion deformity of the proximal interphalangeal (PIP) joint of the toe, with hyperextension of the metatarsophalangeal (MTP) and distal interphalangeal (DIP) joints. Progressive PIP joint flexion deformity typically leads to compensatory hyperextension of the MTP and DIP joints. This makes the PIP joint prominent dorsally. Pain occurs due to rubbing of the prominence against the patient's shoe. The deformity is flexible at first but usually becomes fixed over time. When the deformity is flexible, various procedures can be utilized that involve manipulation of the involved tendons. However, when the deformity is fixed, PIP fusion or joint replacement is often required. Implants available for this purpose include the Weil-Carver™ Hammertoe Implant (Biomet®, Inc., Warsaw, Ind.), Flexible Digital Implant (Tornier, Inc. Edina, Minn.), SHIP Implant (Sgarlato Labs, Campbell Calif.), Digital Compression Screw (BioPro®, Port Huron Mich.), Smart Toe™ Intramedullary Memory Implant (Memometal Inc., Memphis Tenn.) and StayFuse™ Intramedullary Fusion Device (Tornier, Inc. Edina, Minn.).

SUMMARY OF THE INVENTION

In an embodiment, a bone joining device suitable for joining a first bone piece to a second bone piece is disclosed. A female component comprises a first elongated stem portion comprising a first end, a first top opposite the first end, and an opening that extends axially from the first top toward the first end, the first elongated stem portion suitable for insertion from the first eng longitudinally into a surface of the first bone piece. A male component comprises a second elongated stem portion comprising a second end and a second top, the second elongated stem portion suitable for insertion from the second end longitudinally into a surface of the second bone piece, and a connector extending from the second top, the connector comprising an elongated shaft, a top of shaft near the second top, and a distal end. The connector and the second elongated stem portion are a single piece. The connector is capable of insertion into the opening in the first elongated stem portion and locking therein.

In another embodiment, the device is capable of promoting fusion of the first bone piece to the second bone piece.

In another embodiment, the surface of the first bone piece and the second bone piece is a cut surface.

In another embodiment, the device is suitable for joining or fusing: two vertebrae, two cut bones from a joint on a lesser toe; a joint on a finger, a diaphysis of a bone; or a diaphysis of a shortened metatarsal.

In another embodiment, the first stem portion is suitable for insertion from the first end longitudinally into a cut surface of a resected phalanx, metatarsal or metacarpal, or a cut diaphysis, and the second stem portion is suitable for insertion from the second end longitudinally into a cut surface of a resected phalanx, metatarsal or metacarpal, or a cut diaphysis.

In another embodiment, the opening in the first elongated stem portion of the female component is a cavity comprising a wall, a closed distal end and an open proximal end, and the connector is elongated and fits within the cavity.

In another embodiment, the cavity of the female component and the connector of the male component comprise a circular, oval, rectangular, square, hexagonal or octagonal cross section.

In another embodiment, the connector is a bendable connector allowing the adjustable positioning of the connector in an angular direction in relation to the second top. The connector may be capable of being bendably positioned in relation to the second top when coupling to the female component. The connector may be capable of being bent at an angle of at least about 10 degrees, at least about 45 degrees, at least about 90 degrees, or at least about 120 degrees in a forward direction or a reverse direction in relation to the second top.

In another embodiment, the first elongated stem portion or the second elongated stem portion is cylindrical conical or a combination thereof, and comprises a spiraling thread or a continuous spiraling thread. The spiraling thread may spiral clockwise. The pitch of one rotation of the spiraling thread may be less than 1 mm. The spiraling thread may allow self-tapping or self-threading of the first elongated stem portion into the first bone piece of the second elongated stem portion into the second bone piece.

In another embodiment, the connector of the male component further comprises a ring formed around the distal end about the same shape and about the same diameter or less than the diameter of the cavity of the female component and the female component further comprises one or more insertable retaining pins extending through the wall of the wall of the female component into the cavity such that the connector can be secured in the cavity when the distal ring of the connector is inserted past a position of one or more retaining pins. The cavity of the female component is cylindrical with a cylindrical wall and the connector further comprises a ring formed around the distal end about the same diameter or greater than the diameter of the cylindrical cavity, and a cross slit directed axially from the distal end toward the proximal end of the connector, thereby forming a spring collet, and the cylindrical cavity further comprises one or more retaining pins extending into the cylindrical cavity such that, when the connector is inserted into the cylindrical cavity, the spring collet is compressed when the ring of the connector encounters the one or more retaining pins and the spring collet transitions to a less compressed state when inserted beyond a position of one or more retaining pins. The cavity of the female component is cylindrical with a cylindrical wall and the connector further comprises a ring formed around the distal end having a diameter larger than the diameter of the cylindrical cavity and a cross slit directed axially from the distal end toward the proximal end of the connector, thereby forming a spring collet, and the cylindrical cavity further comprises at least a first ring-shaped recess circumscribing the cylindrical wall near the distal end such that, when the connector is inserted into the cylindrical cavity, the spring collet is compressed until the ring encounters the at least first ring-shaped recess, where the at least first ring-shaped recess accommodates a less compressed diameter of the ring and the spring collet transitions to a less compressed state. The cavity of the female component is cylindrical with a cylindrical wall and the connector further comprises at least two shaft-rings surrounding and protruding from the shaft, one shaft-ring closer to the distal end of the shaft than the other shaft-ring, wherein the circumference of the shaft-rings is less than the circumference of the cylindrical cavity in the first elongated stem portion of the female component, and the cylindrical cavity in the first elongated stem portion of the female component further comprises a slot circumscribing the cylindrical wall near the proximal end of the cavity, the slot further comprising a c-ring fitting therein, the c-ring protruding into the cavity when relaxed, wherein the c-ring is capable of receding into the slot when the connector is inserted into the cavity and a ring on the shaft encounters the c-ring, and the c-ring is further capable of becoming relaxed and re-protruding into the cavity after the ring on the shaft passes the c-ring, providing space in the cavity to accommodate the relaxed c-ring. The connector of the male component comprises a shaped shaft, wherein the shaped shaft comprises a plurality of axially deposed indentations or ridges on at least one portion of the shaped shaft, the first elongated stem portion of the female component comprises an indentation at least partially circumscribing the first top such that the at least one knob fits into the at least one hole and protrudes into the cavity, wherein, when the connector is inserted into the cavity in the first elongated stem portion of the female component, the at least one knob protruding into the cavity encounters the connector of the male component and retracts out of the cavity until the connector is inserted further in the cavity and the knob encounters an indentation or a gap between two ridges, allowing the knob to protrude into the cavity of the female component into a space between the wall and the connector created by the indentation or gap.

In another embodiment, the ring may comprise an edge on the side opposite of the distal end of the connector of the male component. The edge of the ring may be designed to prevent movement of the connector out of the cavity of the female component after insertion past the one or more retaining pins, the at least first ring-shaped recess, the c-ring, or the o-ring. The edge may be substantially perpendicular to the wall of the cavity of the edge forms an acute angle with the perimeter of the connector.

In another embodiment, the connector of the male component is inserted into the cavity of the female component past the one or more retaining pins, the at least first ring-shaped recess, the c-ring, or the o-ring, the connector continues to be capable of being bendably positioned in relation to the second top.

In another embodiment, the connector of the male component comprises a groove along the length of the connector. The first elongated stem portion of the female component further comprises a pin hole through the side of the first elongated stem portion, the pin hole comprising an anti-rotation pin capable of fitting in the groove of the connector when the connector is inserted into the cavity of the female component, wherein the anti-rotation pin prevents rotation of the connector in relation to the first elongated stem portion when the anti-rotation pin is in the groove of the connector.

In an embodiment, the device comprises a first mark on the first top of the female component and a second mark on the second top or the connector of the male component, the marks aligning at the desired position of the male component and the female component when the connector of the male component is inserted into the cavity of the female component.

In another embodiment, the connector of the male component and the wall and the cavity of the female component have a cylindrical shape, wherein the cylindrical connector fits into the cylindrical cavity, or the connector of the male component and the wall and cavity of the female component have a hexagonal shape, wherein the hexagonal connector fits into the hexagonal cavity, or the top of the shaft of the connector comprises a hexagonal formation and the first top of the female component comprises a hexagonal recess, wherein the hexagonal formation fits into the hexagonal recess when the connector is inserted into the cavity.

In another embodiment, the device comprises one or more materials selected from a group consisting of titanium, an allow of titanium with about 6% aluminum and about 4% vanadium, nitinol, stainless steel, and poly ethyl ethyl ketone (PEEK).

In an embodiment, a tool for facing a bone surface and reaming a hole into an intramedullary canal of the bone comprises an elongate shank having a proximal end and a distal end. The distal end terminates in a first shaping drill end terminating in a first point, the first shaping drill further comprising a plurality of first ridges having sharp edges immediately proximal to the first point; a first short shaft immediately proximal to the first ridges; a first shoulder wider than the first short shaft immediately proximal to the first short shaft; a first skirt having a first distal surface, wider than the first shoulder immediately proximal to the first shoulder having a flat distal surface; and a first cutout extending from the plurality of first ridges through the first short shaft, the first shoulder, and the first skirt, the first cutout having sharp lateral edges designed to cut through the bone as the tool is rotated and driven therein.

In another embodiment, the reamed hole in the bone accommodates the first elongated stem portion of the female component or the second elongated stem portion of the male component of the device.

In another embodiment, the first shoulder is the approximate diameter or less than the diameter of the first shank.

In another embodiment, the tool comprises a handle or is configured to join a separate handle.

In an embodiment, a driver suitable for screwing the device disclosed above into an intramedullary canal of a bone is disclosed. An elongate shank has a proximal end and a distal end. The distal end comprises a third mark that aligns with the first mark of the female component or the second mark of the male component of the device, such that the third mark aligns with the first mark or the second mark when the distal end properly holds the female component or the male component, respectively.

In another embodiment, the driver comprises a groove in the distal end of the driver, such that the groove accommodates the one or more retaining pins of the female component of the device when the distal end properly holds the female component.

In another embodiment, the driver comprises a handle or is configured to join a separate handle.

In an embodiment, a package comprises the aforementioned device, at least one tool, and at least one driver, wherein the device, the at least one tool, and the at least one driver are sterile.

In another embodiment, the package comprises a handle configured to join the at least one tool or the at least one driver, wherein the handle is sterile.

In an embodiment, a method of joining or fusing a first bone piece with a second bone piece in a living vertebrate is disclosed. The bone joining device is inserted between the first bone piece and the second bone piece such that the two bone pieces are securely joined.

In another embodiment, a surface is faced, and a hole is reamed into the first bone piece or the second bone piece. The first elongated stem portion of the female component is inserted longitudinally into the faced surface of the first bone piece such that the first end is inserted first and the first top is at or slightly below the faced surface of the first bone piece. The second elongated stem portion of the male component is inserted longitudinally into the faced surface of the second bone piece such that the proximal end of the connector is just above the faced surface of the second bone piece. The connector of the male component is inserted into the opening in the first elongated stem portion of the female component.

In another embodiment, the first bone piece is faced and reamed with the fool, or the second bone piece is faced and reamed with the tool.

In another embodiment, the first elongated stem portion of the female component is inserted longitudinally into the faced surface of the first bone piece with the driver, or the second elongated stem portion of the male component is inserted longitudinally into the faced surface of the second bone piece with the driver.

In another embodiment, the bone pieces are a first vertebrae and a second vertebrae; two adjoining phalanges; a phalanx and an adjoining metacarpal; a phalanx and an adjoining metatarsal; bone pieces separated by a fracture or osteotomy of a bone diaphysis; bone pieces separated by an osteotomy that shortens the bone; bone pieces separated by an osteotomy of a lesser metatarsal that shortens the bone; or from a single metatarsal bone that has been subjected to an osteotomy of the diaphysis.

In another embodiment, the bone pieces are in a mammal, in the foot of a mammal, in the hand of a mammal; in a human, in a foot of a human, or in a hand of a human.

In another embodiment, the foot exhibits a hammertoe, mallet toe, curly toe, or claw toe condition.

In another embodiment, the connector is a bendable connector allowing the adjustable positioning of the connector in an angular direction in relation to the second top of the male component, the method further comprising adjusting the position of the connector in relation to the second top of the male component to form a preferred angle of flexion between the two bone pieces.

In another embodiment, the connector of the male component is bent to the preferred angle of flexion between the two bone pieces before insertion of the connector into the opening of the first elongated stem portion of the female component, or the connector of the male component is bent to the preferred angle of flexion between the two bone pieces after partial insertion of the connector into the opening of the first elongated stem portion of the female component.

In another embodiment, the connector of the male component is bent to the preferred angle of flexion between the two bone pieces with the driver.

In another embodiment, the connector of the male component is inserted into the opening in the first elongated stem portion of the female component comprising aligning a first mark on the female component and a second mark on the male component.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1A:
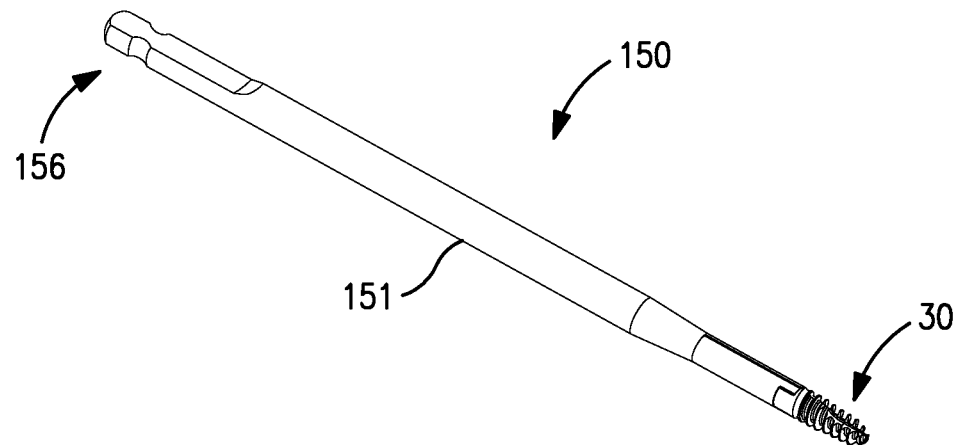
FIG. 1A is a perspective view of one embodiment of a distal driver shown with distal screw attached.
Figure 1B:
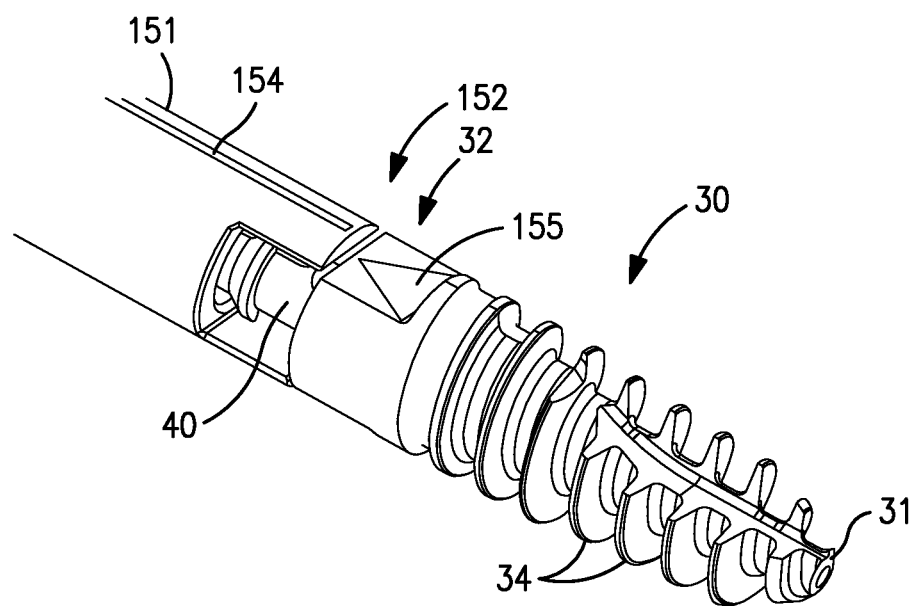
FIG. 1B is an enlarged view of one embodiment of a distal driver shown with distal screw lined-up line (on the drive) and arrow (on the screw) for loading in the driver (on the drive) and arrow (on the screw) for loading in the driver.
Figure 1C:
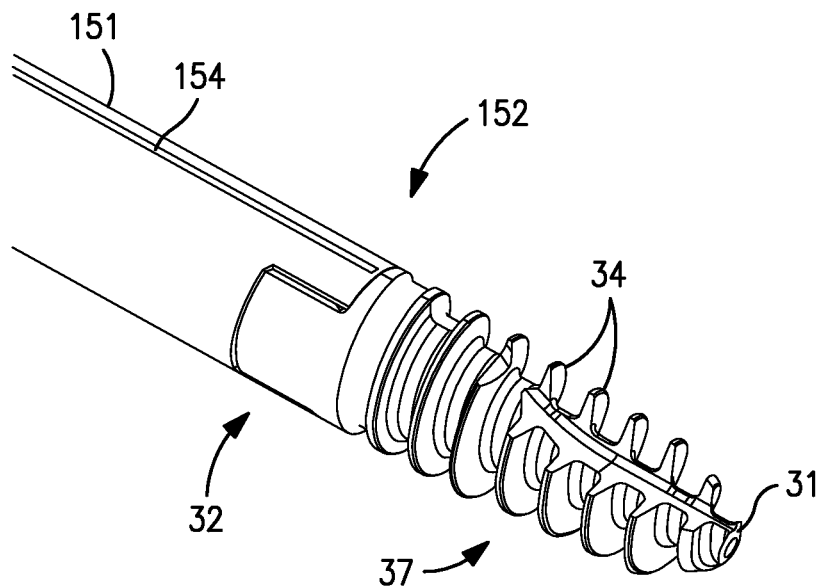
FIG. 1C is an enlarged view of one embodiment of a Distal screw fully loaded in the driver.
Figure 1D:
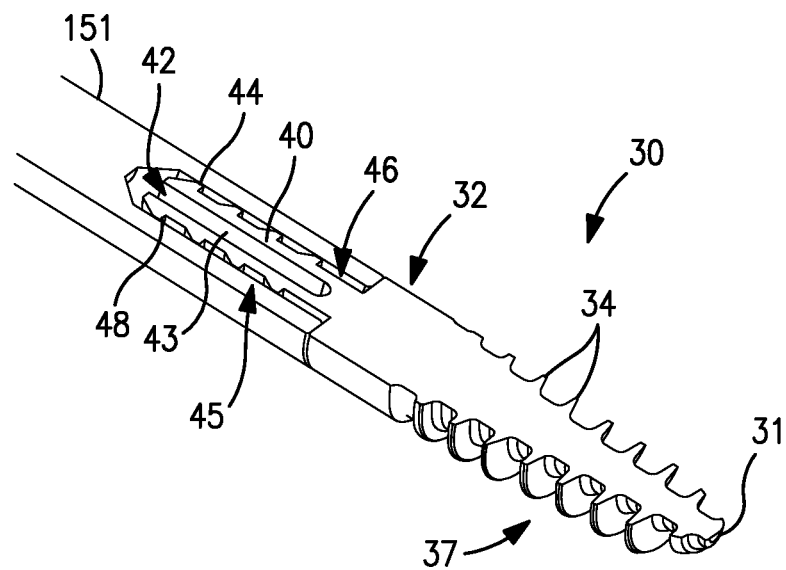
FIG. 1D is a top cross-section view of one embodiment of the screw and driver.
Figure 1E:
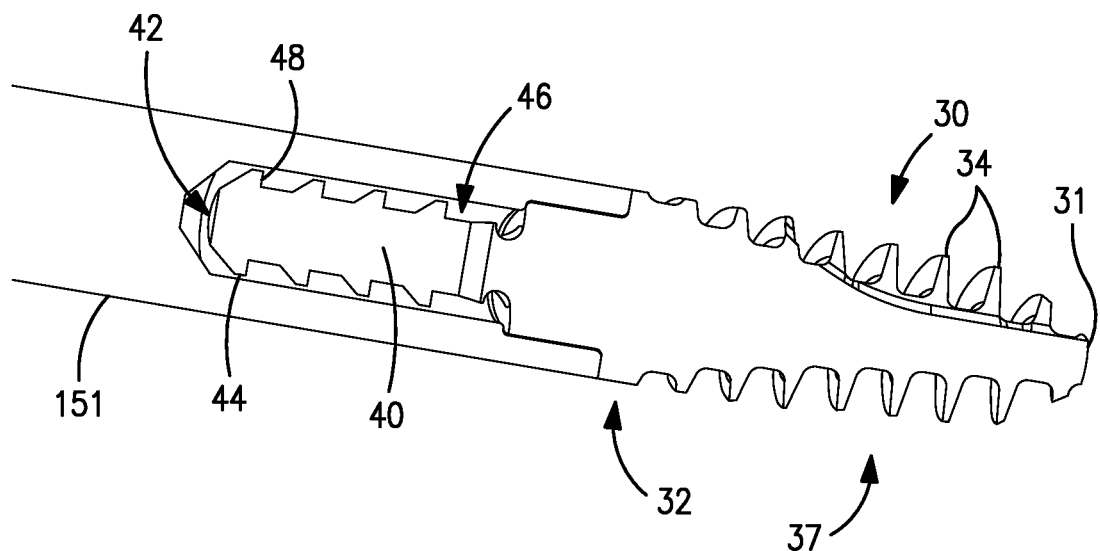
FIG. 1E is a front cross-section view of one embodiment of the screw and driver.
Figure 1F:
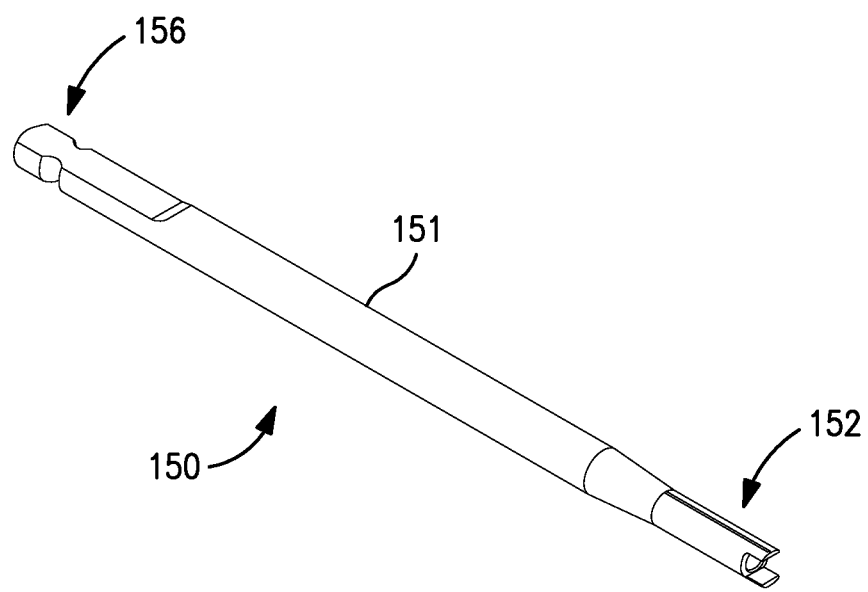
FIG. 1F is a perspective view of one embodiment of a distal driver.
Figure 1G:
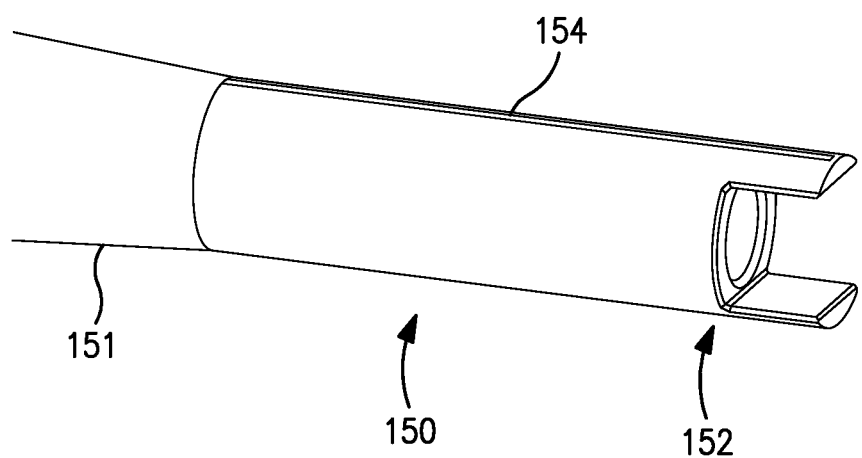
FIG. 1G is an exploded view of one embodiment of the tip of a distal driver.
Figure 2A:
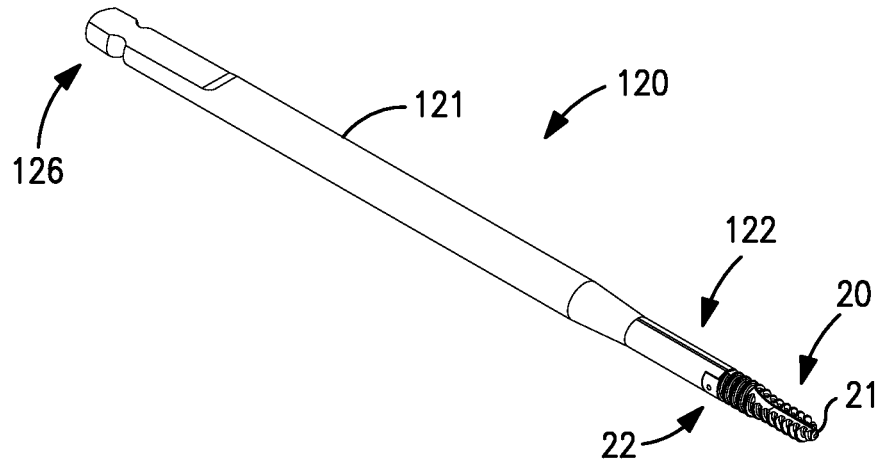
FIG. 2A is a perspective view of one embodiment of a proximal driver with the screw loaded in the driver.
Figure 2B:
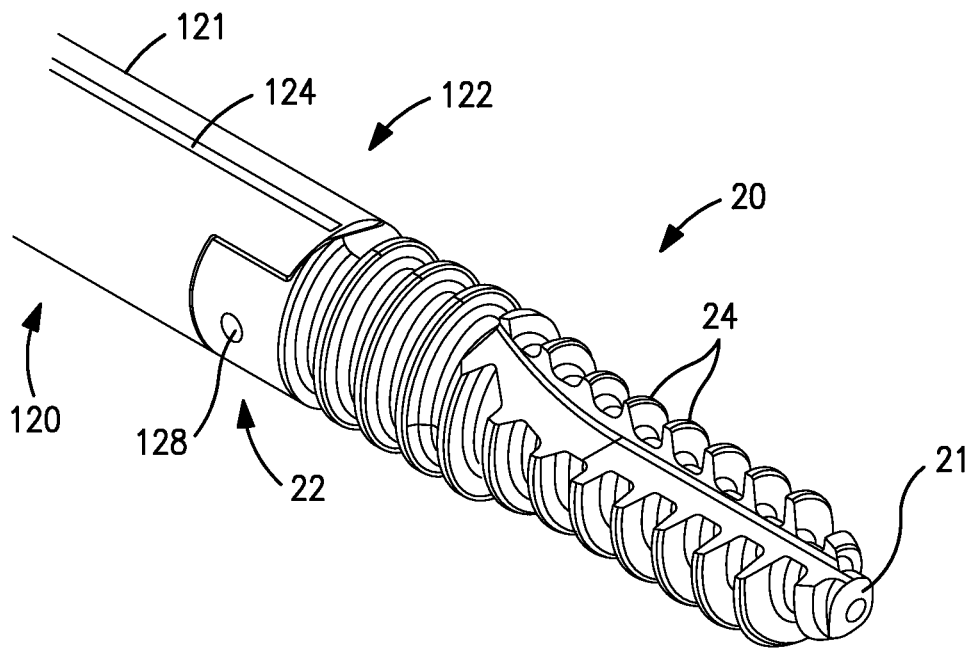
FIG. 2B is an enlarged view of one embodiment of a proximal driver with the screw loaded in the driver.
Figure 2C:
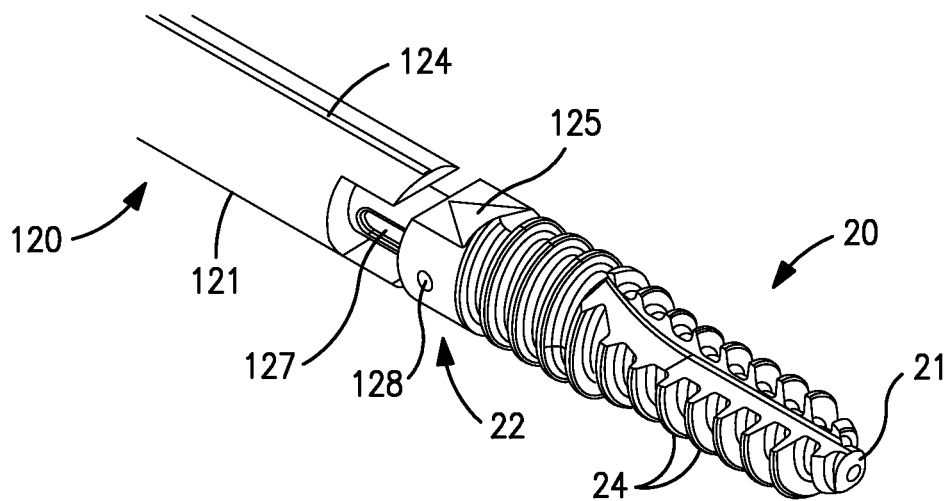
FIG. 2C is an enlarged perspective view of one embodiment of a proximal screw lined-up with the line on a driver and the arrow on the screw head, and showing grooves in the driver protrusion for the retaining pins.
Figure 2D:
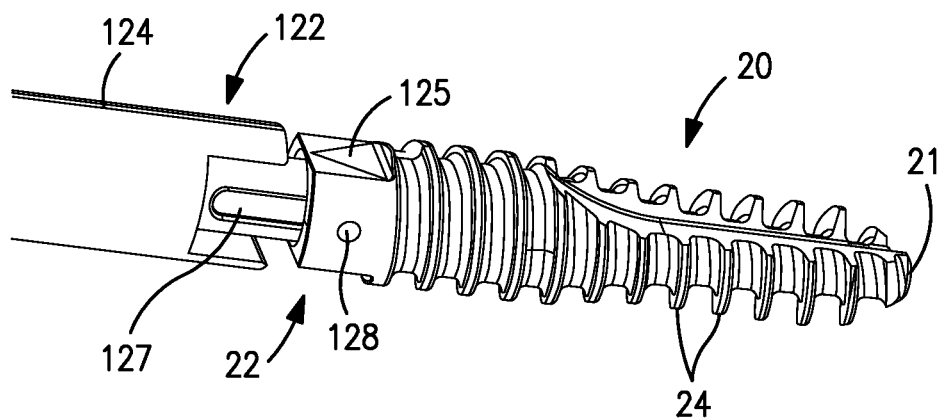
FIG. 2D is an enlarged view of one embodiment of a proximal screw lined-up with the line on a driver and the arrow on the screw head, and showing grooves in the driver protrusion for the retaining pins.
Figure 2E:
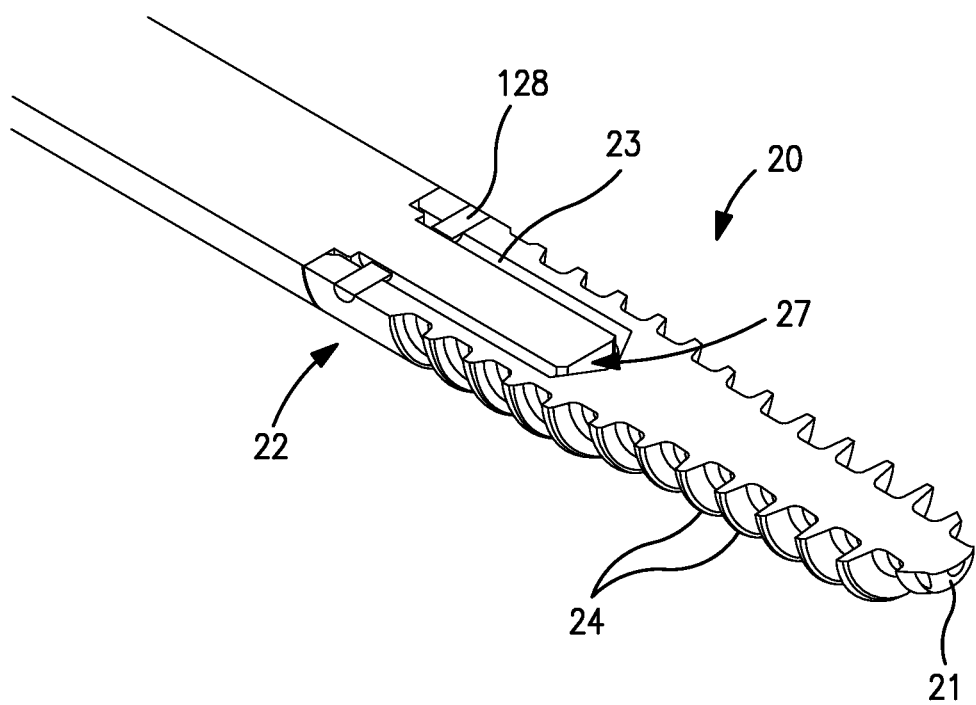
FIG. 2E is a top cross-section of one embodiment of a driver and screw tip.
Figure 2F:
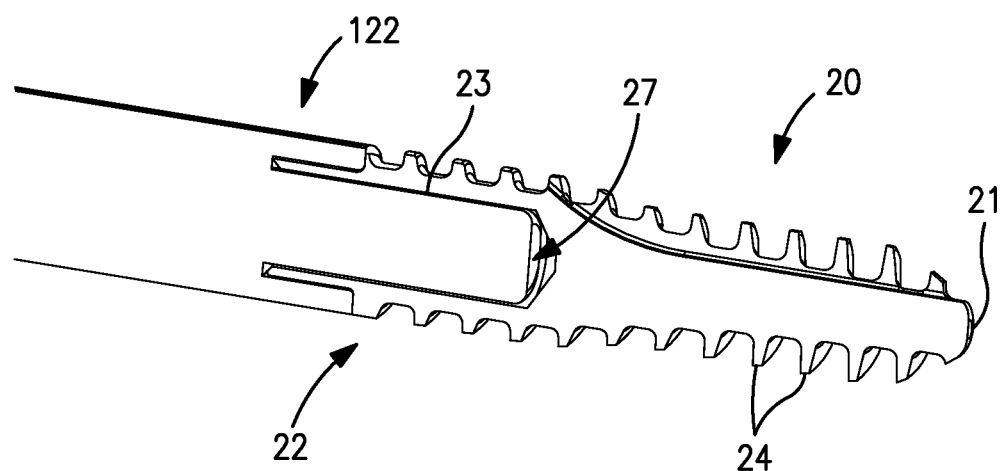
FIG. 2F is a front cross-section of one embodiment of a driver and screw tip.
Figure 2G:
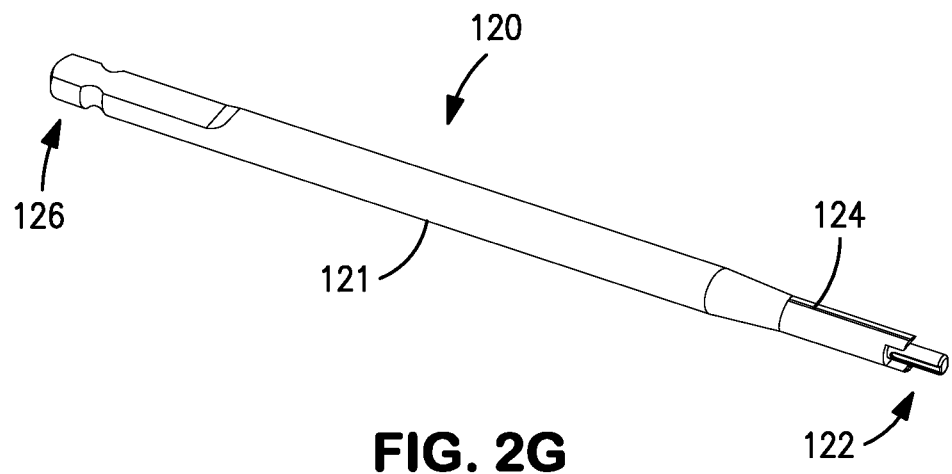
FIG. 2G is a perspective view of one embodiment of a proximal driver.
Figure 2H:
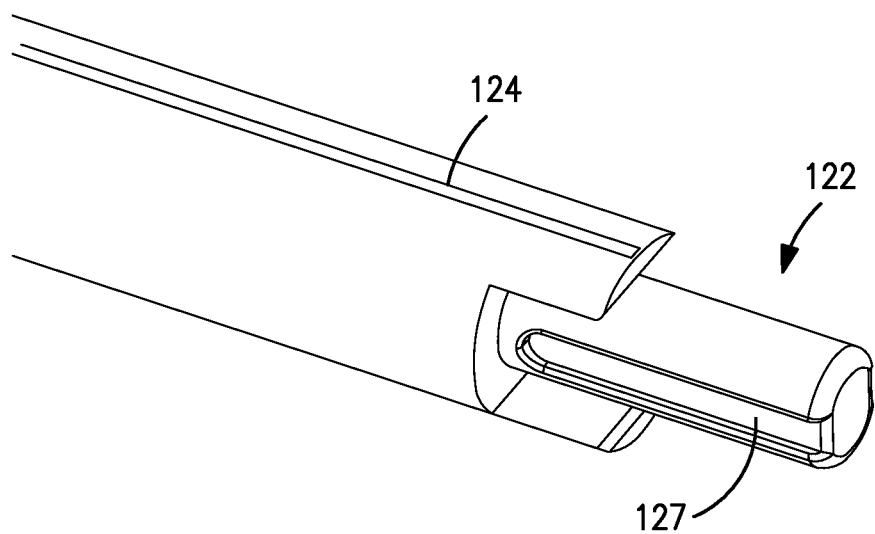
FIG. 2H is an enlarged view of one embodiment of the tip of a proximal driver.
Figure 3A:
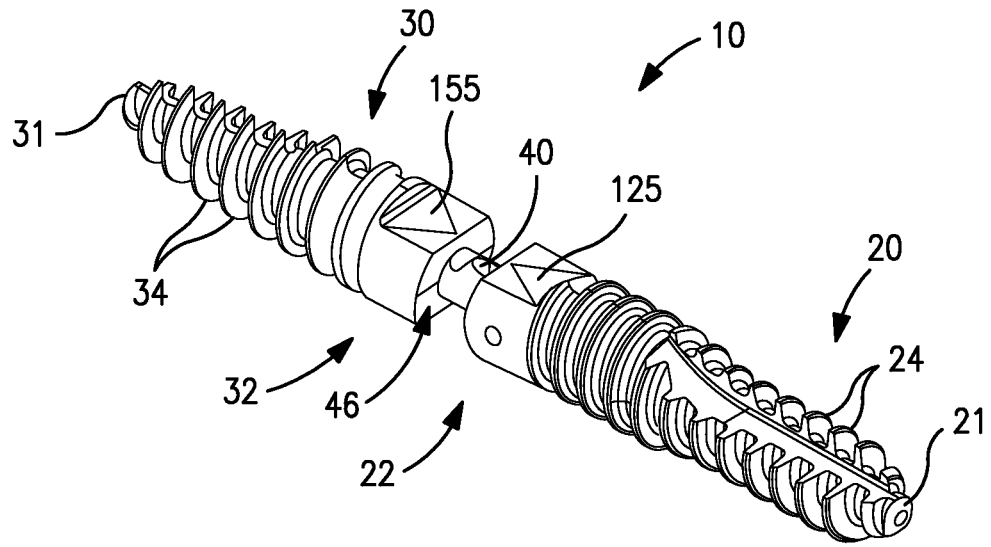
FIG. 3A is a perspective view of one embodiment of an implant with a female component and a partially inserted male component with a split ratcheting tongue held in place by two pins of the female component, where the arrows on the screw heads aid in the lining-up of the screw.
Figure 3B:
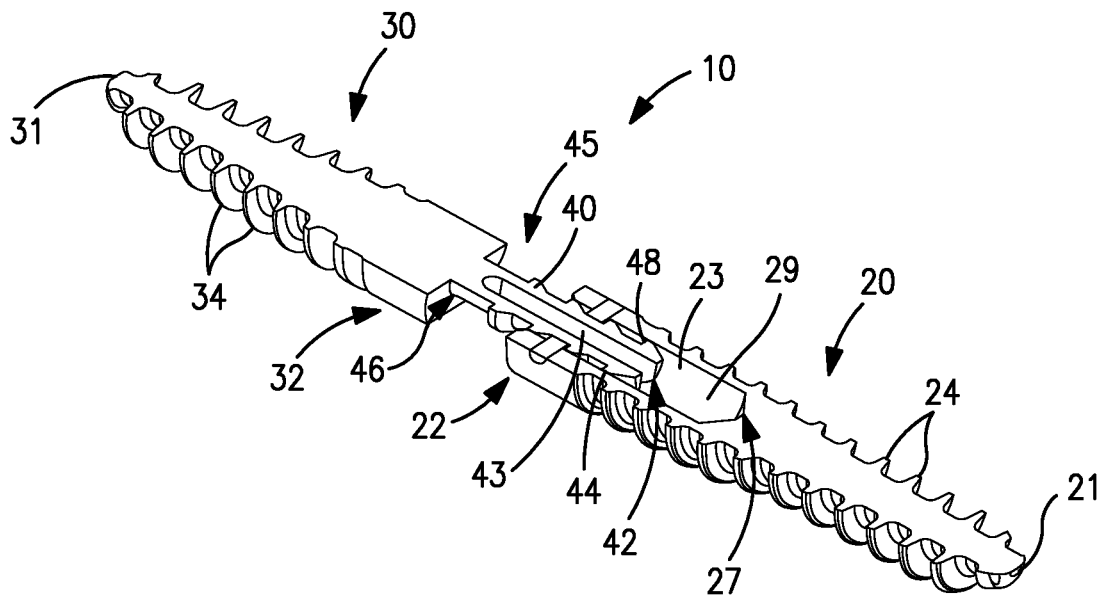
FIG. 3B is top cross-section of one embodiment of an implant with a female component and a partially inserted male component with a split ratcheting tongue held in place by two pins of the female component.
Figure 3C:
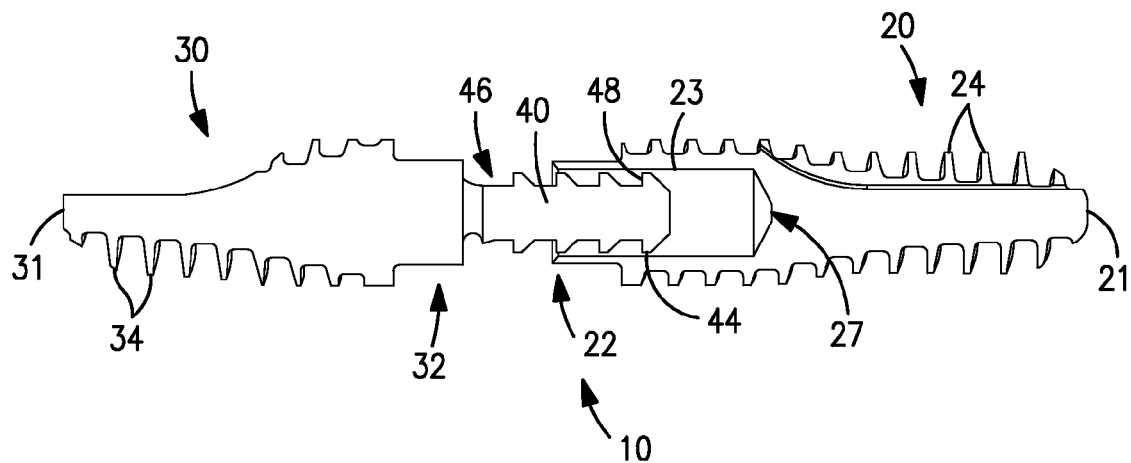
FIG. 3C is a front cross-section of one embodiment of an implant with a female component and a partially inserted male component with a split ratcheting tongue.
Figure 3D:
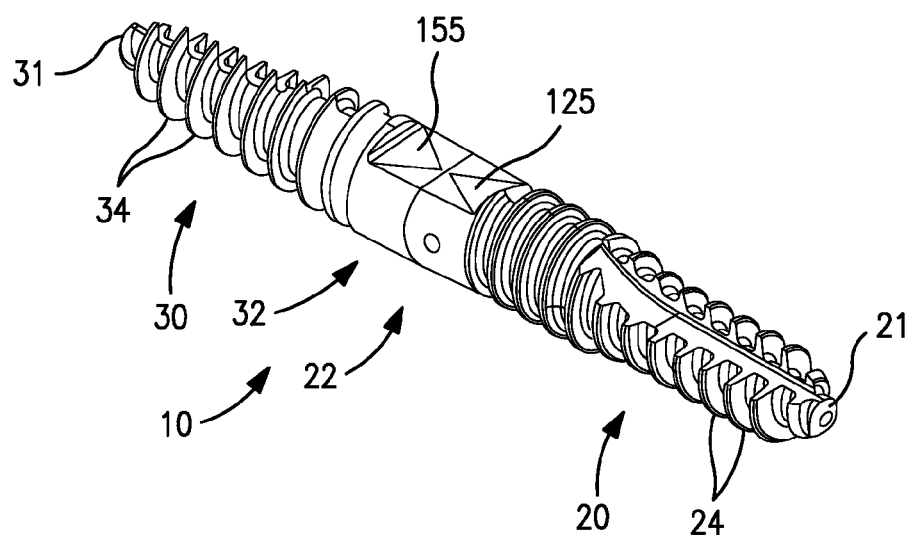
FIG. 3D is a perspective view of one embodiment of an implant with a female component and a fully inserted male component with a split ratcheting tongue held in place by two pins of the female component, where the arrows on the screw heads aid in the lining-up of the screw.
Figure 4A:
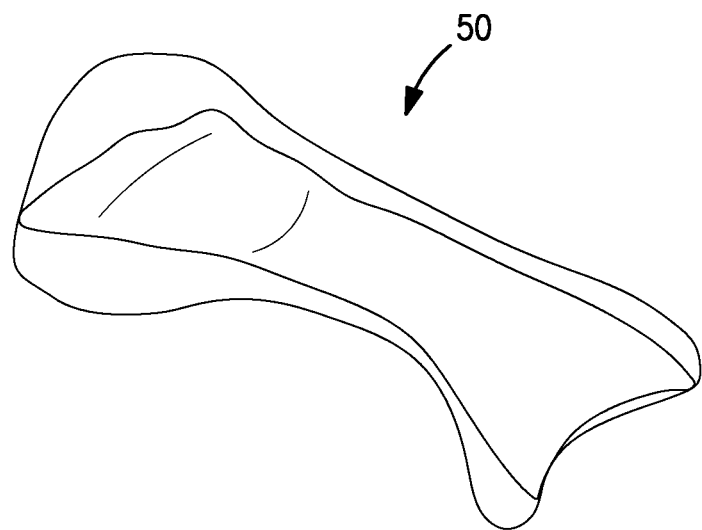
FIG. 4A is a perspective view of one embodiment of a proximal bone of the toe joint.
Figure 4B:
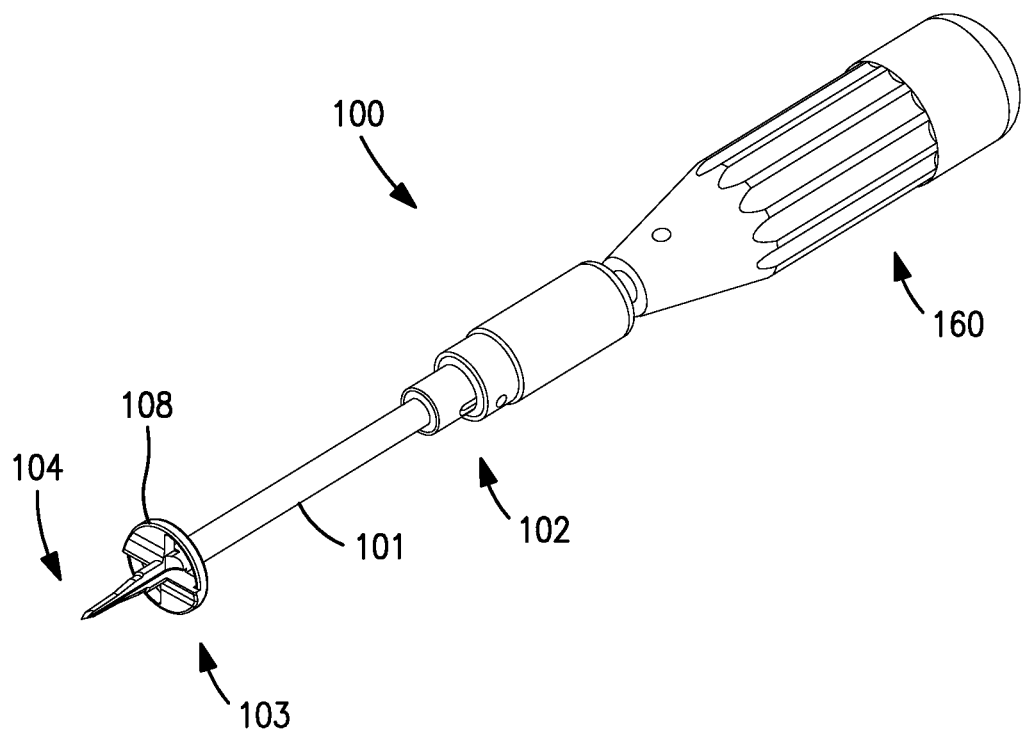
FIG. 4B is a perspective view of one embodiment of a proximal reamer with a Mini A-O Connection and a Mini A-O handle. The depicted embodiment of the reamer shaft can also be used with a power drill with standard Jacobs chuck.
Figure 4C:
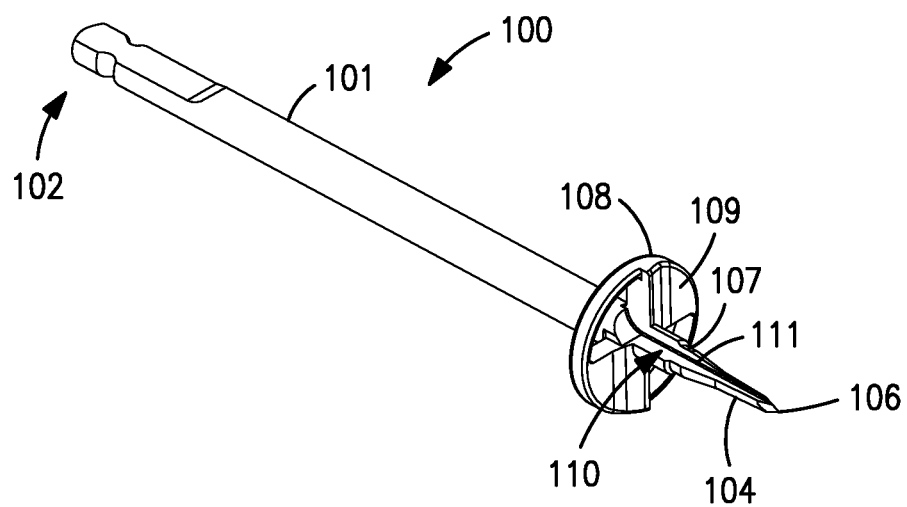
FIG. 4C is a perspective view of one embodiment of a proximal reamer without a handle.
Figure 4D:
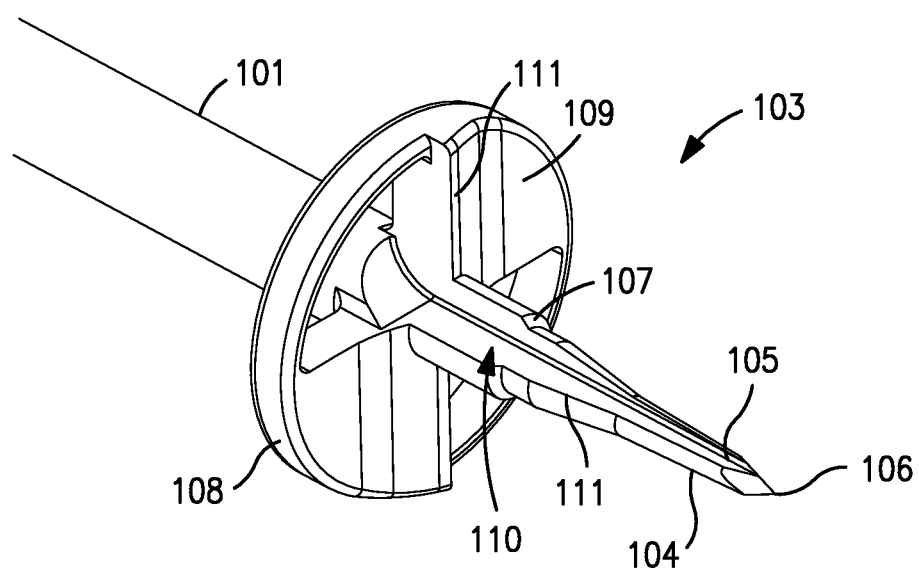
FIG. 4D is an enlarged view of one embodiment of a proximal reamer head that makes a hole equivalent to the core diameter/shape of the proximal screw and also faces-off the bone face in preparation of placing (screwing) the implant into the bone, for an all-in-one operation.
Figure 4E:
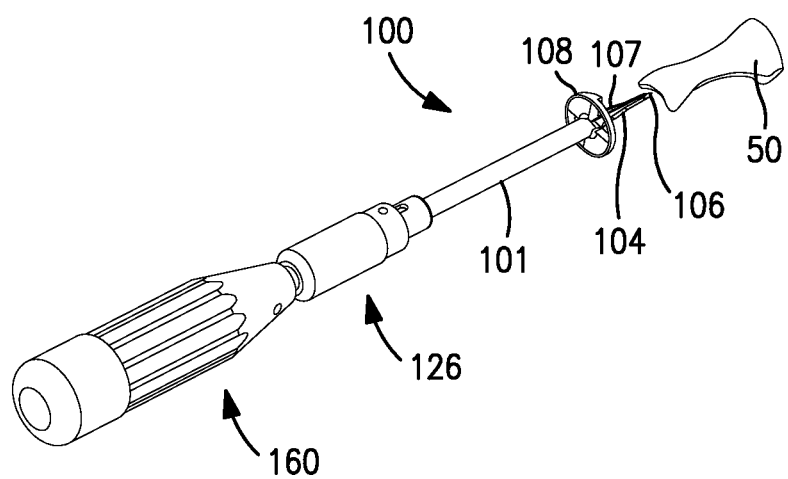
FIG. 4E is a perspective view of one embodiment of a proximal reamer in position to drill/ream and face-off the proximal bone.
Figure 4F:
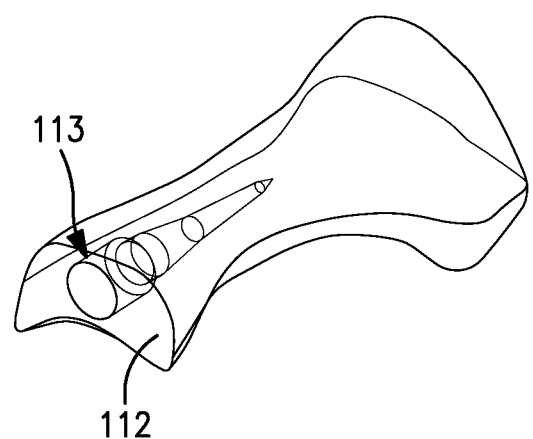
FIG. 4F is a perspective view of one embodiment of a completed drilled/reamed hole profile and the squarely faced-off proximal bone face.
Figure 5A:
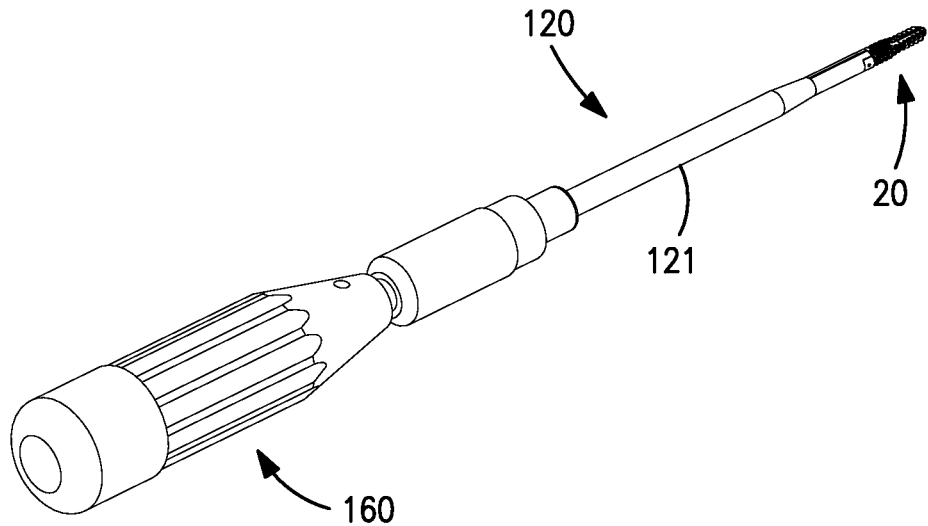
FIG. 5A is a perspective view of one embodiment of a proximal driver with the proximal screw lined-up and partially loaded on the driver just prior to insertion of the screw into the proximal bone.
Figure 5B:
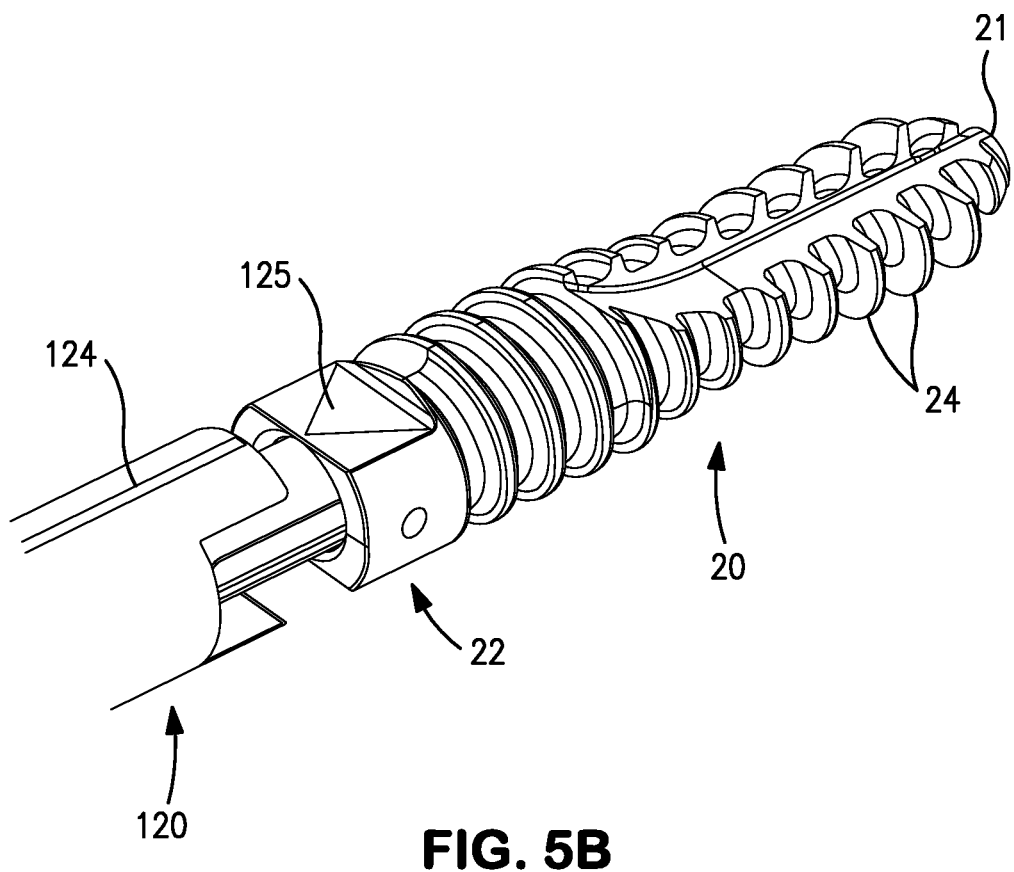
FIG. 5B is an enlarged view of one embodiment of the proximal driver with the proximal screw lined-up and partially loaded on the driver.
Figure 5C:
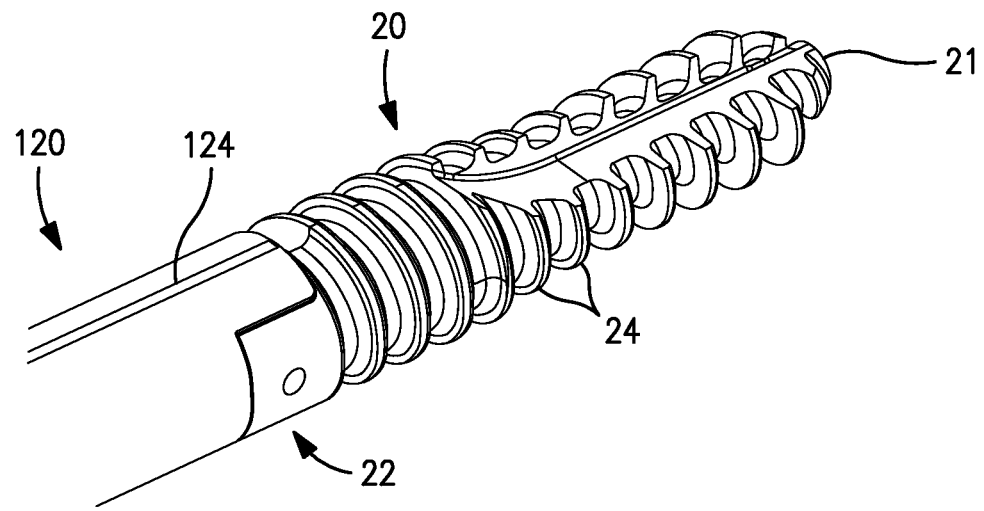
FIG. 5C is an enlarged view of one embodiment of the proximal driver with the proximal screw lined-up and fully loaded on the driver.
Figure 5D:
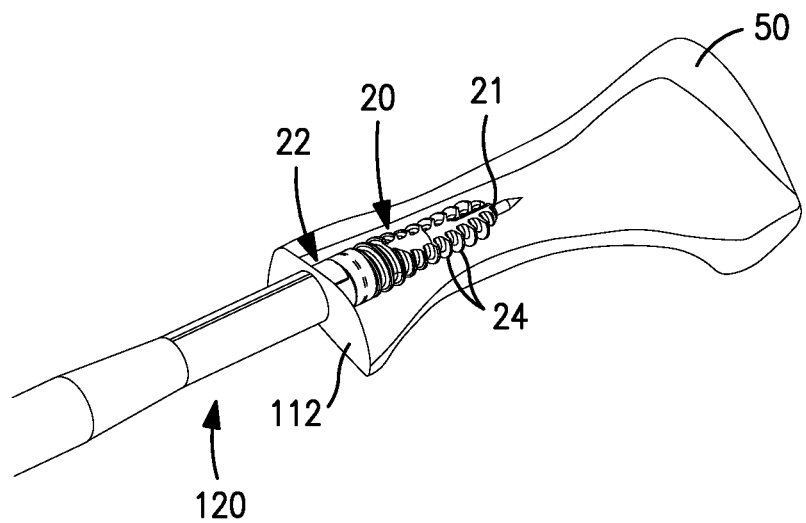
FIG. 5D is a perspective view of one embodiment of the proximal screw screwed in place with the driver in the proximal bone.
Figure 5E:
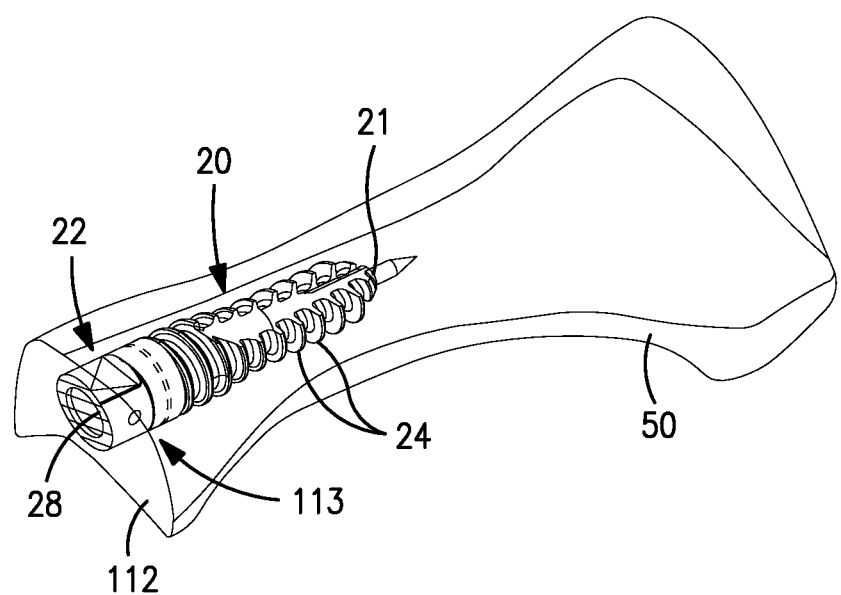
FIG. 5E is an enlarged view of one embodiment of the proximal screw in the bone and flush with the faced end of the bone.
Figure 6A:
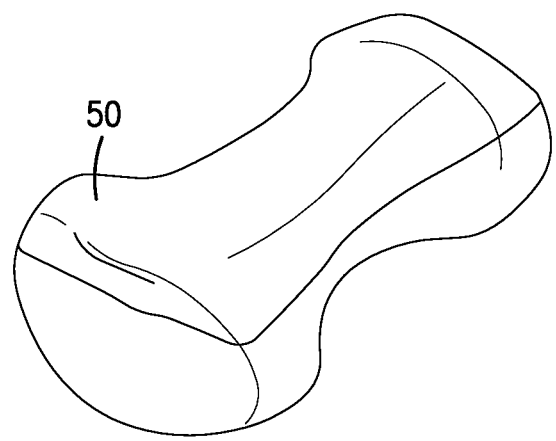
FIG. 6A is a perspective view of one embodiment of the distal bone, where the lower left face is the mating surface of the proximal bone.
Figure 6B:
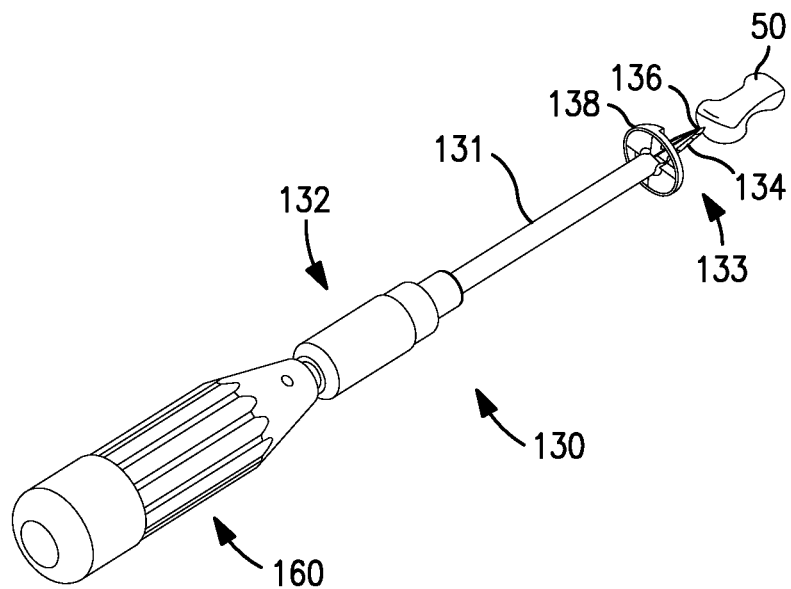
FIG. 6B is a perspective view of one embodiment of the distal drill/reamer in position to drill/ream and face-off the distal bone.
Figure 6C:
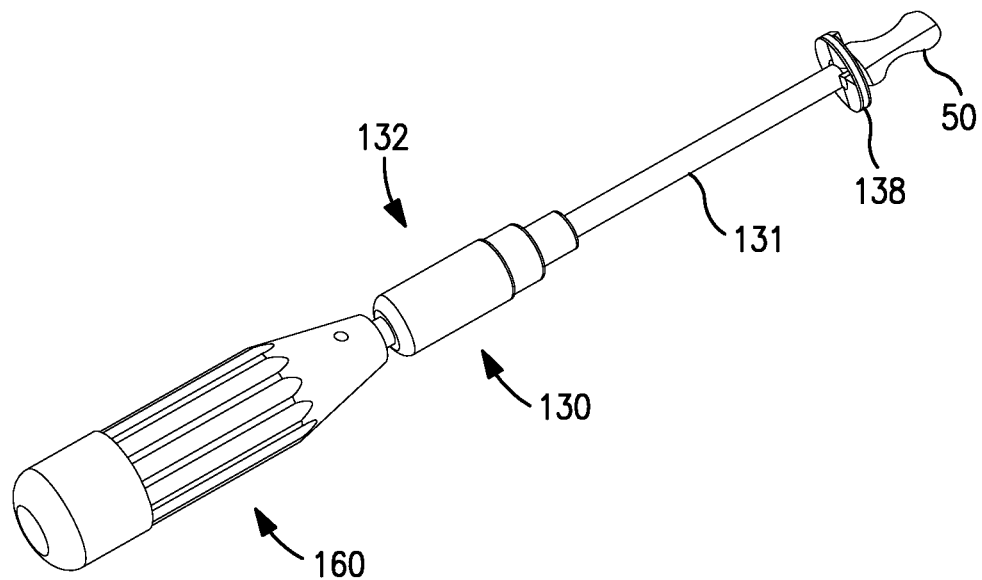
FIG. 6C is a perspective view of one embodiment of the reamer in the distal bone.
Figure 6D:
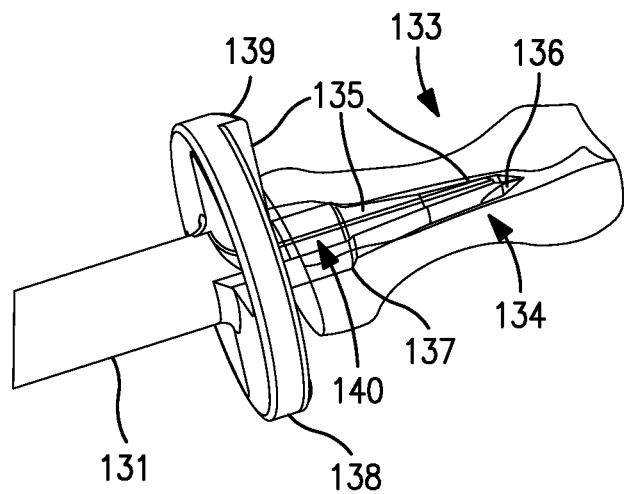
FIG. 6D is an enlarged view of one embodiment of the reamer in the distal bone.
Figure 6E:
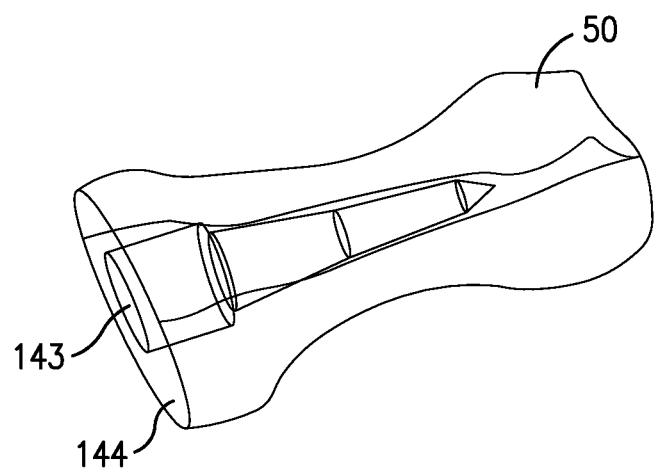
FIG. 6E is a perspective view of one embodiment of a completed hole and face-off of the distal bone.
Figure 7A:
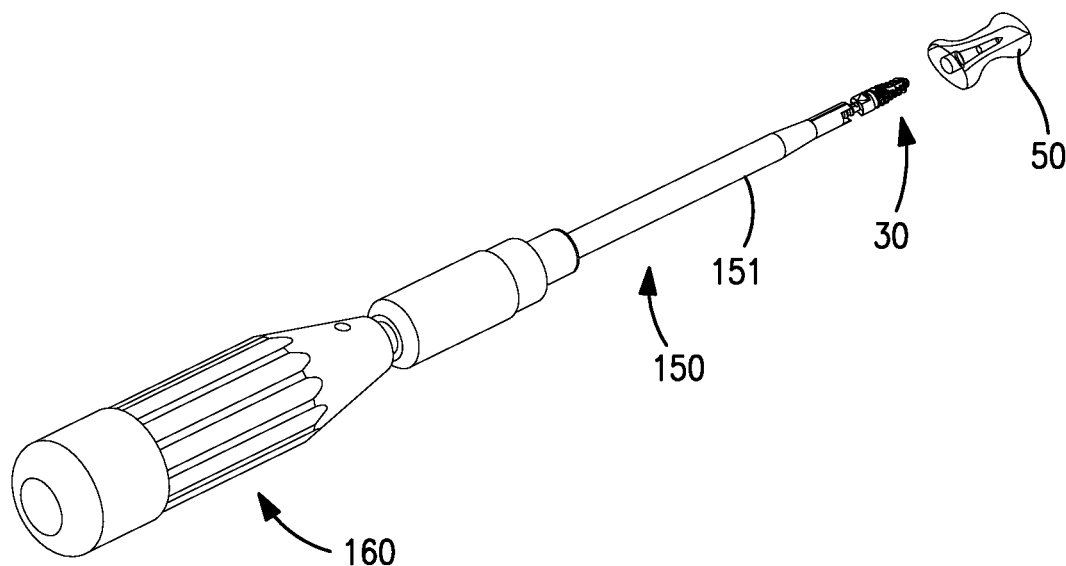
FIG. 7A is a perspective view of one embodiment of the distal screw lined up on the distal driver, ready for loading and insertion.
Figure 7B:
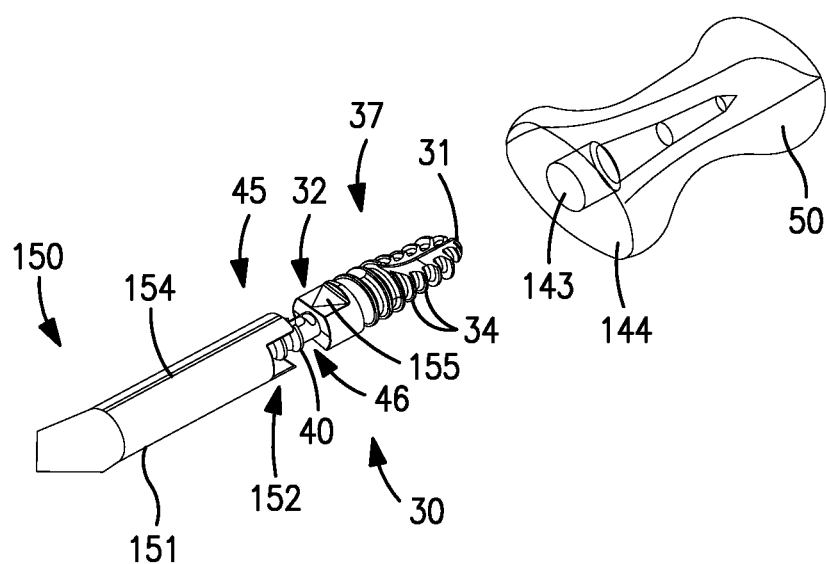
FIG. 7B is an enlarged view of one embodiment of the distal screw lined-up (line on the driver and arrow on the screw head) on the driver.
Figure 7C:
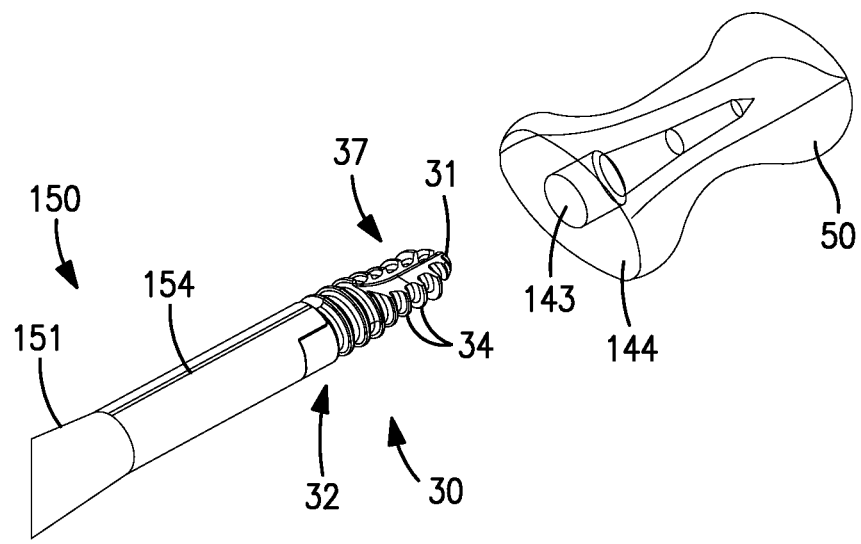
FIG. 7C is an enlarged view of one embodiment of the distal screw fully inserted in the driver.
Figure 7D:
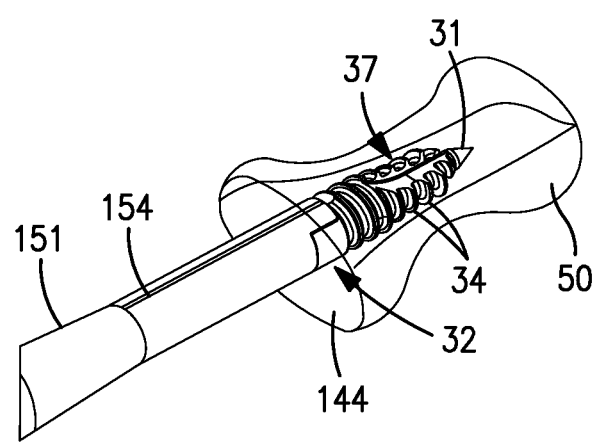
FIG. 7D is a perspective view of one embodiment of the screw screwed into the distal bone.
Figure 7E:
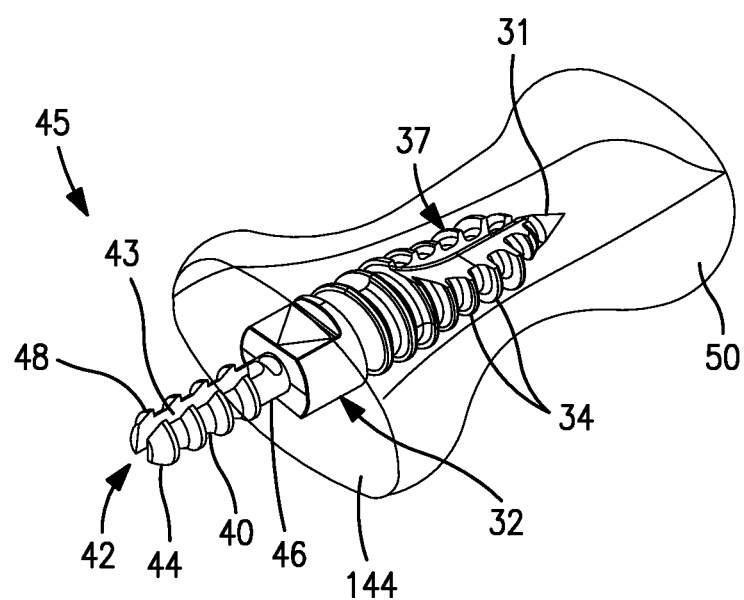
FIG. 7E is a perspective view of one embodiment of the screw in the distal bone, where the screw head edge is flush with the bone face. From this position, the distal screw tongue can be bent if an angle between the bone sections is desirable.

The inventors have developed a bone joining device that allows two bones to be joined. Various embodiments provide a bone joining device having a streamlined design that is less costly to manufacture as compared to conventional devices. Also provided in various embodiments are drill/reamers designed to drill, ream and face-off the bone all in one operation. Various driver embodiments are designed to aid in the holding and aligning of the screws prior to screwing these into the bone, to be low profile so as to eliminate a need for a larger than maximum screw diameter drill hole to insert the screw into the bone, and, optionally, bend the distal screw tongue if an angle between the implant screws is desired. Various embodiments of drivers or drill/reamers are designed to be used with standard connections (e.g., Mini A-O) or can be used with a power drill with, for example, a Jacobs Chuck. Various designs presented herein will assist in simplifying their use, for example, having markings on the screw heads and the drivers for alignment purposes.

In some embodiments, the application is directed to a bone joining device suitable for joining a first bone piece to a second bone piece. The device comprises a first component and a second component, wherein the first component comprises a first elongated stem portion comprising a first end and a first top opposite the first end, the first elongated stem portion suitable for insertion from the first end longitudinally into a surface of the first bone piece, and the second component comprises a second elongated stem portion comprising a second end and a second top, the second elongated stem portion suitable for insertion from the second end longitudinally into a surface of the second bone piece. The device further comprises a connector extending from the second top. The connector is capable of joining with the first component and locking therewith.

The connector may join with the first component by any means known in the art. Non-limiting examples of such joining means include knobs, clamps, teeth, glues, Velcro® and staples. In some embodiments, the first component is a female component and the second component is a male component, wherein the first elongated stem portion of the female component further comprises an opening that extends axially from the first top toward the first end; and the connector comprises an elongated shaft, a proximal end, a top of shaft near the proximal end, and a distal end, wherein the connector is capable of insertion into the opening in the first elongated stem portion and locking therein. The figures provide several examples of these devices, as detailed below.

The device is generally useful for joining any two bone pieces, for example two vertebrae or two halves of a broken bone. In some embodiments, the device is particularly useful for joining or fusing cut surfaces of bones, in particular the cut ends of long bones, especially fingers or toes, e.g., for joining or fusing a joint on a lesser toe, for example to treat hammertoe, claw toe, mallet toe or curly toe. In those embodiments, the first stem portion is suitable for insertion from the first end longitudinally into a cut surface of a resected phalanx, metatarsal or metacarpal, or a cut diaphysis, and the second stem portion is suitable for insertion from the second end longitudinally into a cut surface of a resected phalanx, metatarsal or metacarpal, or a cut diaphysis. The device can also be used to fuse a metatarsal that has been shortened by resection.

Figure 8:
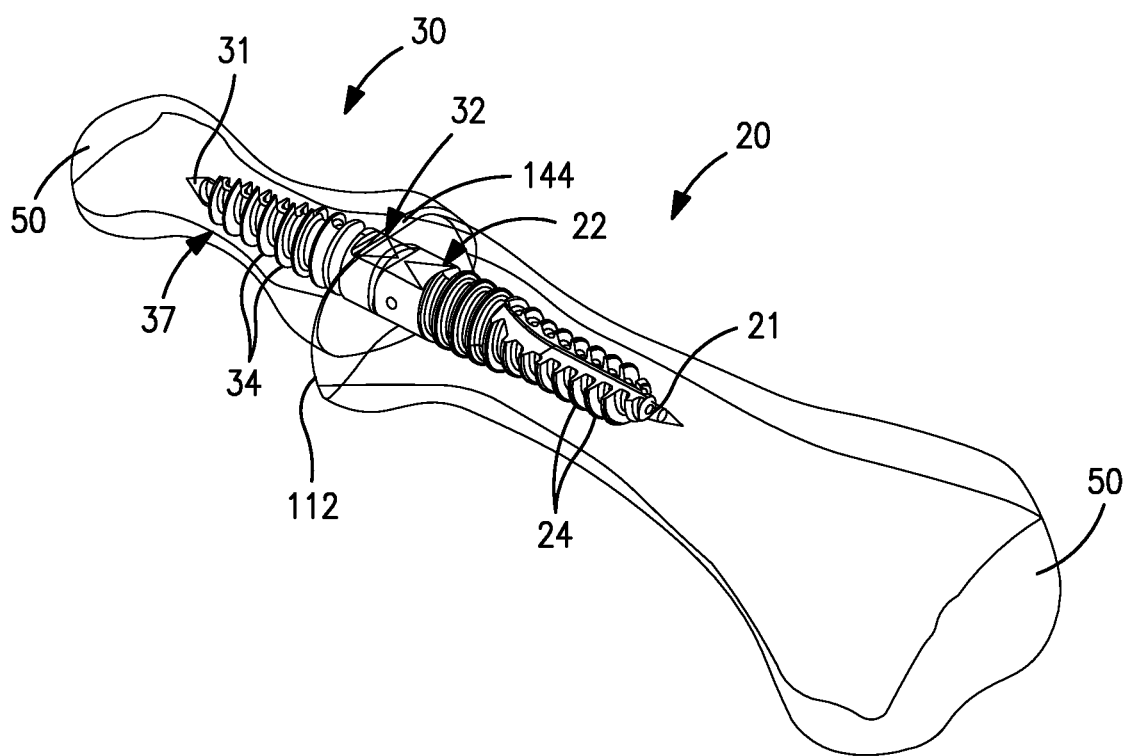
FIG. 8 is a perspective view of one embodiment of the assembled implant in the proximal and distal bones.
Figure 9:
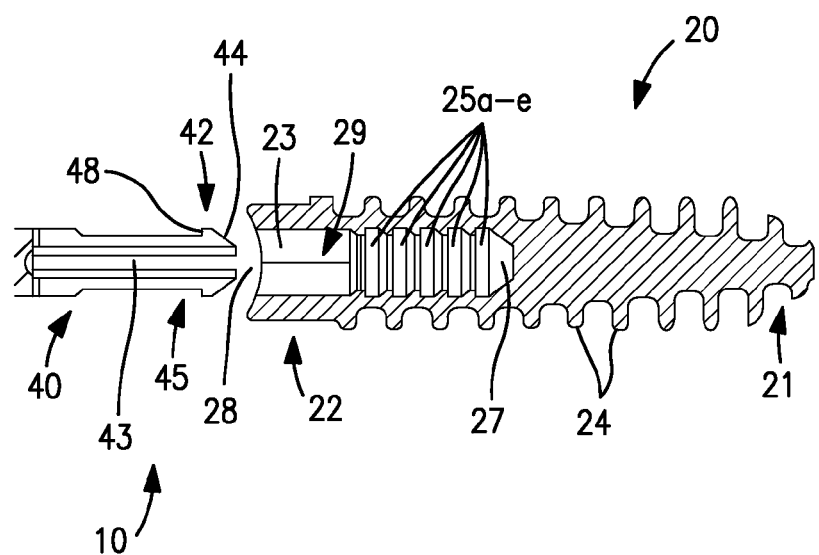
FIG. 9 is a sectional view of one embodiment of the bone joining device showing the female component and a portion of the male component aligned for joining.
Figure 10:
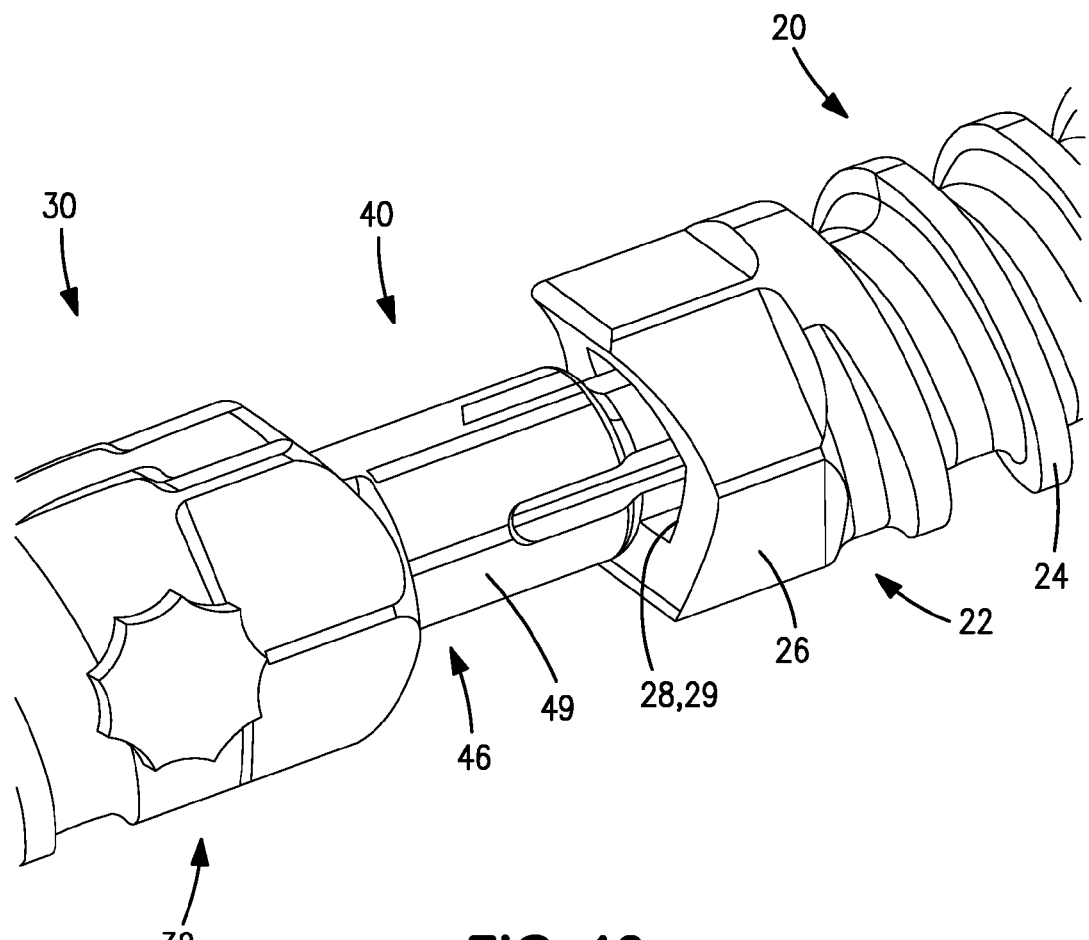
FIG. 10 is an enlarged fragmentary view of one embodiment of the bone joining device after partial insertion of the male component connector into the female component.
Figure 11:
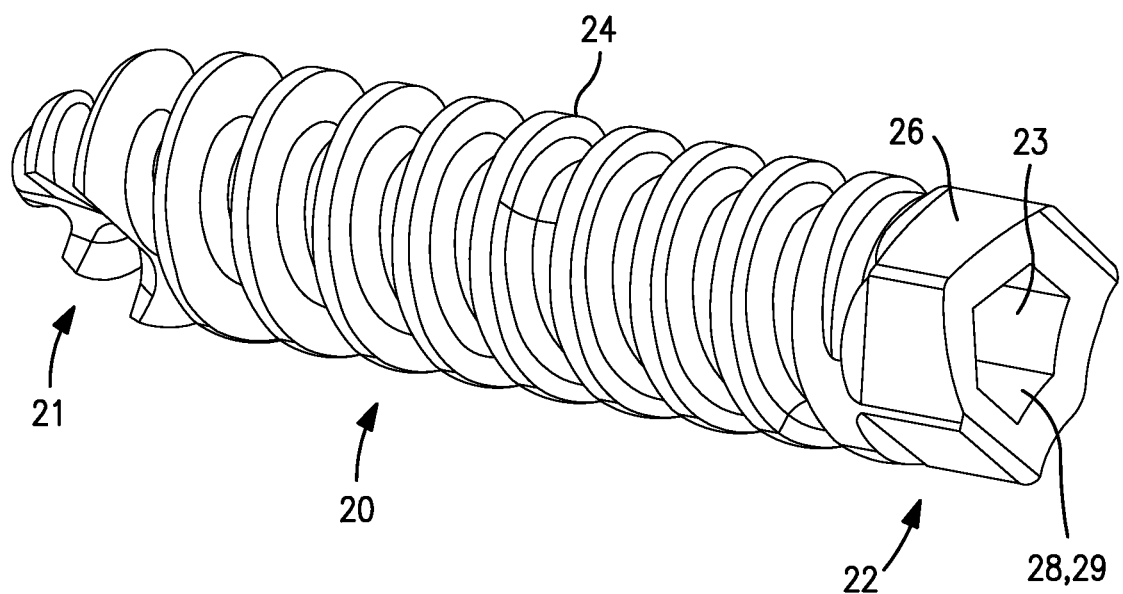
FIG. 11 is a perspective view of one embodiment of the female component of the bone joining device.

Various, non-limiting embodiments of the device are shown in FIG. 3 and FIG. 8, where the bone joining device 10 is provided as a female component 20 and a male component 30.

The female component 20 of this embodiment is an elongated stem, and comprises a first end 21, a first top 22 and a cylindrical cavity 29, comprising a cylindrical wall 23, a closed distal end 27 and an open proximal end 28. The illustrated female component 20 also comprises a continuous spiraling thread 24 on the exterior of the component, suitable for screwing the component into a bone 50. The female component 20 can comprise one or more retaining pins 128 in the first top 22, suitable for retention of a connector 40 of the male component 30 or for interfacing with the second groove 127 of the proximal driver 120. The female component 20 is also referred to herein as the "first elongated stem portion." The cavity and wall can have any shape cross section as defined by the cavity wall, including, for example, circular, oval, rectangular hexagonal and octagonal.

The male component 30 comprises a second elongated stem portion 37 comprising a second end 31 and a second top 32, with the connector 40 extending from the second top 32. The male component 30 is also referred to herein as the "second elongated stem portion." The illustrated second elongated stem portion 37 comprises a continuous spiraling thread 34 on the exterior, where the thread is suitable for screwing the component into a bone 50.

The female component 20 and the male component 30 can independently be cylindrical or conical, or any combination thereof, e.g., cylindrical at the proximal end, transitioning into a conical shape.

While the illustrated embodiments show a spiraling thread as a means to anchor the male component and the female component into the bone, any alternate anchoring means can be used, for example barbs, a shape memory expanding means (e.g., as featured in the Smart Toe™ Implant (Memometal Inc., Memphis Tenn.), or any other anchoring means known in the art.

Where present, the spiraling threads on the device can be of any type known in the art for screwing into a bone. In some embodiments, the spiraling thread is a continuous spiraling thread. In other embodiments, the spiraling thread allows self-tapping and/or self-threading of the first elongated stem portion into the first bone piece and the second elongated stem portion into the second bone piece.

In some embodiments, the continuous spiraling thread 24 and 34 on the female and male components both spiral in the same direction, e.g., clockwise, so that, when the device is screwed into opposing bone surfaces and then joined, the opposing pitch of the threads in the bone prevents the device from unscrewing.

These embodiments are not limited to any particular pitch of one rotation of the continuous spiraling thread. For example, the pitch may be 5 mm or greater, 4 mm, 3 mm, 2 mm, 1 mm, less than 1 mm, or any distance in between these distances.

In some embodiments, the angle of connector 40 is fixed. For example, the angle of the connector 40 can be about 2, about 4, about 6, about 8, about 10, about 12, about 14, about 16, about 18, about 20, about 22, about 24, about 26, about 28, about 30, about 32, about 34, about 36, about 38, about 40 degrees, or more.

In some embodiments, the angle of connector 40 can be changed, for example, through bending. A connector 40 that is bendable can be supplied at an angle of 0 degrees or greater. For example, a connector 40 that is bendable can be supplied at an angle of about 0, about 2, about 4, about 6, about 8, about 10, about 12, about 14, about 16, about 18, about 20, about 22, about 24, about 26, about 28, about 30, about 32, about 34, about 36, about 38, about 40 degrees, or more. A connector 40 that is supplied at a fixed angle, as described above, can be bent to another angle. For example, a connector 40 that is supplied at a fixed angle, as described above, can be bent an additional about 2, about 4, about 6, about 8, about 10, about 12, about 14, about 16, about 18, about 20, about 22, about 24, about 26, about 28, about 30, about 32, about 34, about 36, about 38, about 40 degrees, or more.

In some embodiments, where an angle is necessary between the proximal and distal portions, the ratchet tongue of the male component 30 can be bent at a desired angle using one or both drivers as leverage or a holding device.

Figure 12:
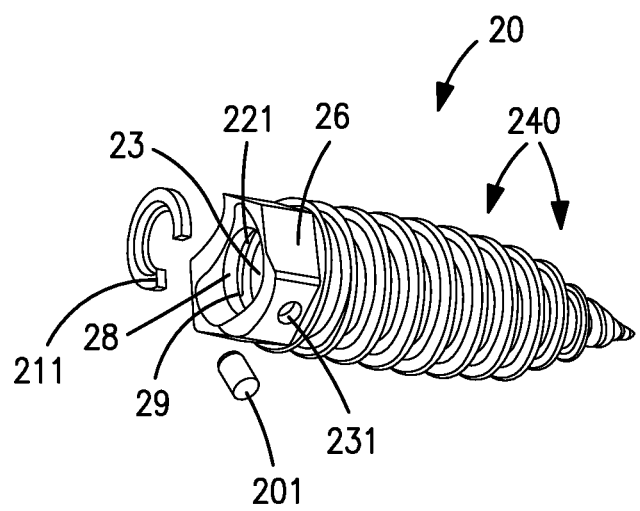
FIG. 12 is an exploded perspective view of one embodiment of the bone joining device.
Figure 13:
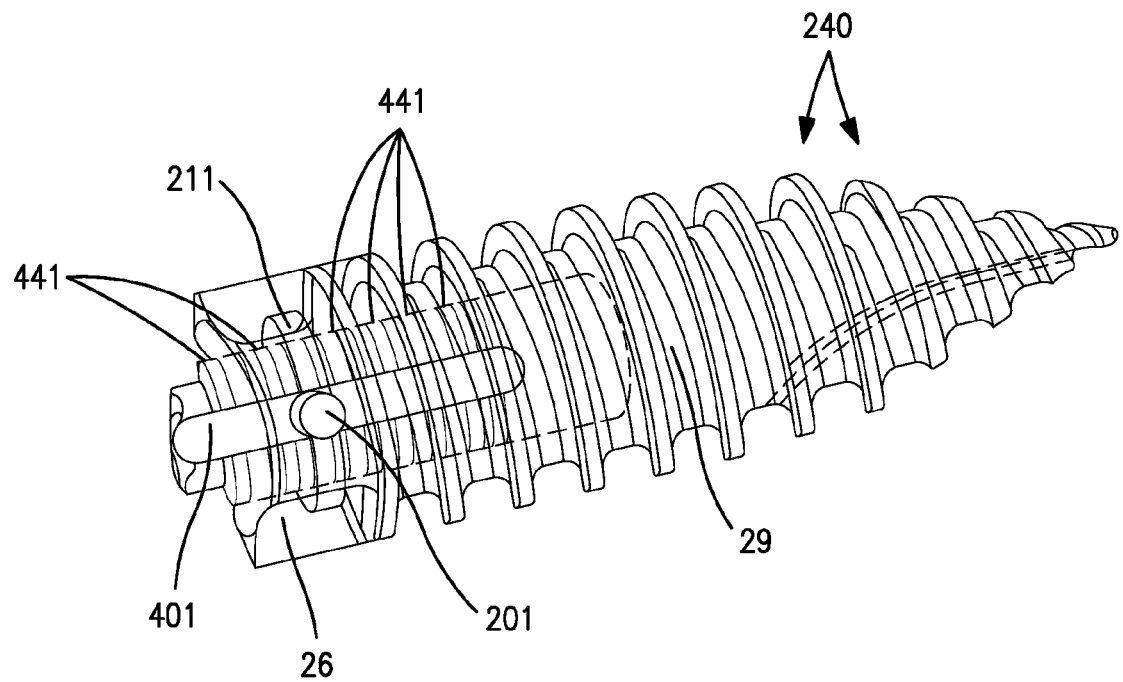
FIG. 13 is a perspective, partial see-through view of one embodiment of the bone joining device after partial insertion of the connector into the female component.
Figure 14:
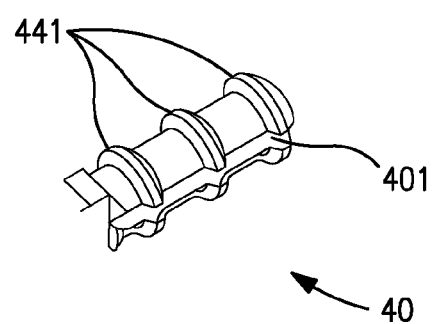
FIG. 14 is an exploded perspective view of one embodiment of the connector of the male component.

In some embodiments, the cylindrical cavity 29 of the female component 20 is designed to receive the connector 40 through the proximal end 28 of the cavity 29. In these embodiments, the connector 40 is elongated and cylindrical. The connector 40 can be of a split ratcheting tongue design or spring collet design that interfaces with retaining pins 128 in the cylindrical cavity 29 of the female component 20. The connector 40 further comprises one or more rings 44 formed around or proximal to the distal end 42 (see e.g., shaft rings 441, as shown in FIG. 14), where the ring 44 has a diameter larger than the separation of retaining pins 128 extending from the cylindrical cavity wall 23 or, alternatively, larger than a ring-shaped extension 211 (see FIG. 12) of the cylindrical cavity wall 23; and cross slits 43 directed axially from the distal end 42 toward the second top 32 of the connector 40, thereby forming a spring collet 45. Where the connector 40 comprises a plurality of rings 44, the connector 40 can be inserted into cylindrical cavity 29 such that successive rings 44 engage a retention mechanism of the cylindrical cavity wall 23, such as one or more retaining pins 128 or recesses 25.

To prevent the connector 40 from being pulled out of the cylindrical cavity 29, the ring 44 can comprise an edge 48 on the side closer to the second top 32 of the connector 40, where the edge is designed to prevent movement of the connector 40 in the proximal direction. In an illustrated embodiment, the edge 48 is substantially perpendicular to the wall 23 of the cylindrical cavity 29. In other embodiments, the edge 48 forms an acute angle with the perimeter of the connector 40.

In some embodiments, the ring 44 can be inserted into cylindrical cavity 29 such that retaining pins 128 can engage the edge 48 of the ring 44 so as to prevent connector 40 from being pulled out of the cylindrical cavity 29.

In some embodiments, to accommodate the connector 40, the cylindrical cavity 29 further comprises at least a first ring-shaped recess 25a circumscribing the cylindrical wall 23 near the distal end such that, when the connector 40 is inserted into the cylindrical cavity 29, the spring collet 45 is compressed until the ring 44 encounters the first recess 25a, where the first recess 25a accommodates a less compressed diameter of the ring 44 and the spring collet 45 transitions to a less compressed state.

In an illustrated embodiment, the wall 23 of the cylindrical cavity 29 can further comprises a second ring-shaped recess 25b circumscribing the cylindrical wall 23 closer to the distal end 27 than the first recess 25a, where the connector 40 can be inserted beyond the first recess 25a, compressing the spring collet 45 until the ring 44 encounters the second recess 25b, where the second recess 25b accommodates a less compressed diameter of the ring 44 and the spring collet 45 transitions to a less compressed state.

The distance between the recesses 25a and 25b in the wall 23 of the cylindrical cavity 29 can be any distance appropriate for the particular application. The distance may be 5 mm or greater, 4 mm, 3 mm, 2 mm, 1 mm, less than 1 mm, or any distance in between these values. In some embodiments, the distance is anywhere from 0.2 mm to 1 mm, for example about 0.6 mm.

In an illustrated embodiment, the wall 23 of the cylindrical cavity 29 can further comprises a third ring-shaped recess 25c circumscribing the cylindrical wall 23 closer to the distal end 27 than the second recess 25b, where the connector 40 can be inserted beyond the second recess 25b, compressing the spring collet 45 until the ring 44 encounters the third recess 25c, where the third recess 25c accommodates a less compressed diameter of the ring 44 and the spring collet 45 transitions to a less compressed state.

In an illustrated embodiment, the wall 23 of the cylindrical cavity 29 can additionally comprises a fourth and fifth ring-shaped recess 25d and 25e circumscribing the cylindrical wall 23 closer to the distal end 27 than the third recess 25c, where the connector 40 can be inserted beyond the third recess 25c, compressing the spring collet 45 until the ring 44 encounters the fourth recess 25d or fifth recess 25e, where the fourth and fifth recess 25d and 25e accommodates a less compressed diameter of the ring 44 and the spring collet 45 transitions to a less compressed state.

In some embodiments, when the female component 20 and the male component 30 are screwed into the bone pieces 50, those two components should rotationally align with each other so that the top of the shaft 46 can fit inside the proximal end of the cylindrical cavity 29. Additionally, when the device is used to fuse a digit, as in e.g., hammertoe treatment, the positioning of the connector 40 in an angular direction should be made in the proper rotational plane, such that the connector 40 can be positioned along an angle that follows the natural flexion of the digit. The identity of the proper alignment of the female and male components can be accomplished by any means, for example by providing marks on the first top 22 and on or near the second top 32 of the connector 40, where the marks align at the desired position of the male component 30 and female component 20 when the ring 44 is in the first recess 25a.

The device may additionally comprise any means to prevent rotation of the connector 40 in relation to the first elongated stem portion 20, and to assure that the male component 30 and female component 20 are properly aligned rotationally. In some embodiments, as illustrated in FIG. 14, the connector 40 comprises a first groove 401 along the length of the connector, and the first elongated stem portion 20 further comprises a pin hole 231 through the side of the first elongated stem portion 20, the pin hole 231 further comprising an anti-rotation pin 201 capable of fitting in the first groove 401 of the connector 40 when the connector 40 is inserted into the proximal end of the cavity 29 of the first elongated stem portion 20. The anti-rotation pin 201 prevents rotation of the connector 40 in relation to the first elongated stem portion 20 when the anti-rotation pin is in the first groove 401 of the connector 40.

In some embodiments, the connector 40 further comprises at least two shaft-rings 441 surrounding and protruding from the shaft. Each shaft ring 441 varies from the other shaft-ring(s) in their proximity to the distal end of the shaft. The circumference of the shaft-rings 441 is slightly less than the circumference of the cylindrical cavity 29 in the first elongated stem portion 20 of the female component. In various embodiments, the connector 40 can have at least two, three, four, five, six, or more shaft rings.

In some embodiments, the cylindrical cavity wall 23 comprises one or more retention pins 128 extending therefrom into the cylindrical cavity 29 of the female component 20. The retention pins 128 can, in some embodiments, extend and retract into or out of the cylindrical cavity 29. When a retention pin 128 is sufficiently extended into cylindrical cavity 29, when the connector 40 is inserted into the cavity 29 and a ring 44 (or one or more shaft-rings 441) encounters the retention pin 128. The connector 40 can compress (e.g., via cross slit 43 or spring collet 45) so as to pass a retention pin 128. Alternatively, or in combination, a retention pin 128 can be extended after a ring 44 passes its position along the cylindrical cavity wall 23. Such process can occur multiple times where there is a plurality of shaft-rings 441. Insertion of the connector 40 into cylindrical cavity 29 can therefore be according to a split ratcheting tongue mechanism. In some embodiments, if the ratcheting tongue does not snap in place in the last ratchet, the implant components can be rotated (e.g., 90°) allowing the pins 128 to slide through the cross slit 43 and engage the last ratchet, ring 44, or shaft-ring 441 after the components are rotated back to their aligned position.

In some embodiments, the cylindrical cavity 29 in the first elongated stem portion of the female component 20 further comprises a slot 221 circumscribing the cylindrical wall 23 near the proximal end 28 of the cavity 29. The slot 221 further comprises a c-ring 211 fitting therein. In some embodiments, the c-ring 211 protrudes into the cavity 29 when relaxed. However, the c-ring 211 expands and recedes into the slot 221 when the connector 40 is inserted into the cavity 29 and a shaft-ring 441 encounters the c-ring 211 and pushes against it. This allows the shaft ring 441 to pass the c-ring 211. After the shaft ring 441 passes the c-ring 211, providing space in the cavity 29 to accommodate the relaxed c-ring, the c-ring 211 becomes relaxed again and contracts, re-protruding into the cavity 29.

In an illustrated embodiment, the top of the shaft 46 of the connector 40 comprises a hexagonal formation 49 and the first top 22 comprises a hexagonal recess 26, where the hexagonal formation 49 fits into the hexagonal recess 26 when the connector 40 is inserted into the cylindrical cavity 29. In other embodiments, the formation and recess can be circular, pentagonal, square or any other shape.

In an alternative configuration, the shaft 70 of the connector 40 is cylindrical, with a plurality (e.g., three) of axially deposed indentations 250a-c, 252a-c on at least one side of the shaft 70. In various embodiments, the connector 40 may be elongate but not cylindrical, e.g., key-shaped, having a plurality of axially deposed ridges, such as, for example, semicircular, or arced ridges. For the embodiment illustrated in FIG. 15, the cylindrical shaft 70 of the connector 40 comprises a second set of three axially deposed indentations 250a-c, 252a-c on opposing sides of the shaft.

Figure 16A:
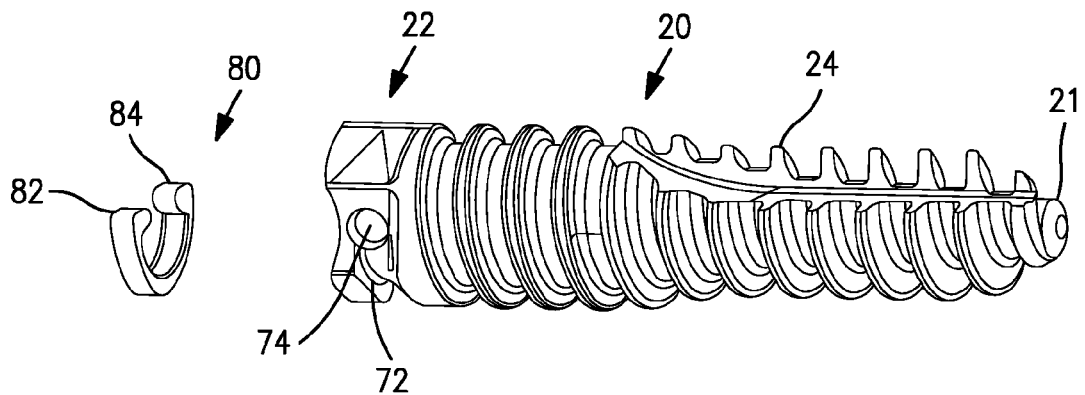
FIG. 16A is a perspective view of one embodiment of a female component of the bone joining device.
Figure 16B:
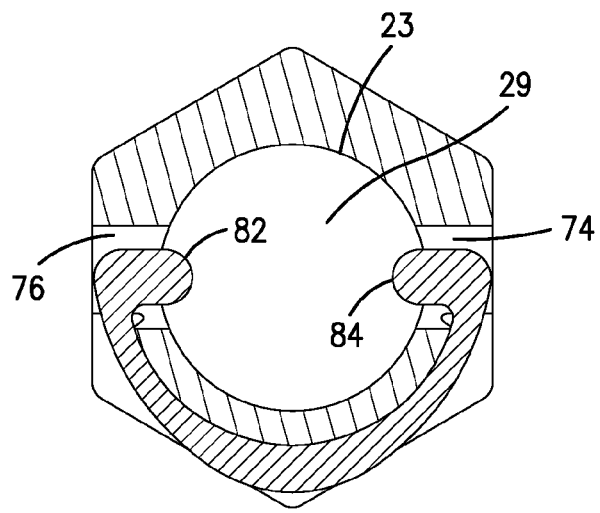
FIG. 16B is a cross-sectional view of one embodiment of a female component of the bone joining device.
Figure 16C:
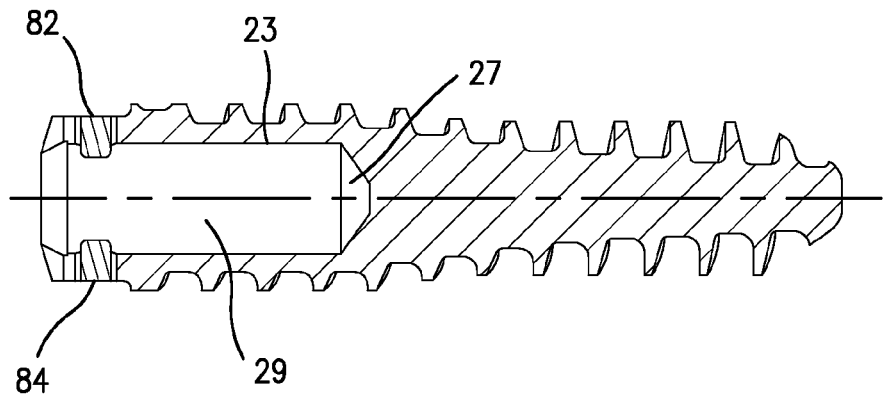
FIG. 16C is a sideways cross-sectional view of one embodiment of a female component of the bone joining device.

As shown in FIG. 16, the female component 20 of this embodiment is an elongated stem, comprising a first end 21, a first top 22, an open proximal end 28 and a cylindrical cavity 29. The cylindrical cavity 29 comprises a cylindrical wall 23, a closed distal end 27 and an open proximal end 28. The illustrated female component 20 also comprises a spiraling thread 24 on the exterior of the component, suitable for screwing the component into a bone.

The female component 20 also comprises an indentation 72 at least partially circumscribing the first top 22, with at least one (here, two) hole 74, 76 passing through the first top 22 into the cylindrical cavity 29.

The female component 20 additionally comprises a knobbed c-ring 80, comprising at least one (here, two) knob protruding inward 82, 84. The knobbed c-ring 80 is configured to fit into the indentation 72 in the first top 22 of the female component 20, such that the knobs fit into the holes 74, 76 and protrude into the cylindrical cavity 29.

In use, the shaft 70 of the connector 40 is inserted into the open proximal end 28 and into the cylindrical cavity 29 of the female component 20, where the distal end 42 of the shaft 70 encounters the knobs 82, 84 of the knobbed c-ring 80, which are protruding into the cylindrical cavity 29. As the shaft 70 of the connector 40 is pushed further into the cylindrical cavity 29, the distal end 42 of the shaft 70 pushes on the knobs 82, 84, expanding the knobbed c-ring 80 such that the knobs 82, 84 are pushed out of the cylindrical cavity 29 to accommodate the shaft 70, until the knobs 82, 84 encounter the first indentations 250c,f, allowing the knobs to move back into the cylindrical cavity 29 in the space created by the indentations, such that the knobbed c-ring 80 compresses back to its original shape. To prevent the connector 40 from being pulled out of the cylindrical cavity 29, the indentations 250 can comprise an edge 480 on the side closer to the distal end 42 of the connector 40, where the edge is designed to prevent movement of the connector 40 in the proximal direction after encountering the indentation 250. In an illustrated embodiment, the edge 480 is substantially perpendicular to the wall 23 of the cylindrical cavity 29. In other embodiments, the edge 480 forms an acute angle with the perimeter of the shaft 70. When the shaft 70 of the connector 40 continues to be pushed further into the cylindrical cavity 29, the knobbed c-ring 80 again expands as the area between the first indentations 250c,f and the second indentations 250b,e pushes the knobs 82, 84 out of the cylindrical cavity 29, until the knobs 82, 84 encounter the second indentations 250b,e. This continues until the knobs 82, 84 are at the indentations most proximal to the male component 30, when the device is seated in its final position. At some point before the device is in its final position, the desired angle of flexion between the connector 40 and the male component 30 is made and set by, e.g., bending to a desired angle, as appropriate.

The various steps described above can be performed in any order, i.e., before or after the insertion into either or both bone pieces. It should also be understood that the described embodiments are exemplary, and any appropriate modifications can be made to the devices described above. For example, the knobbed c-ring can instead be an o-ring, or can comprise one, or any number of knobs in conjunction with a matching number of aligning sets of axially deposed indentations. Additionally, the knob or knobs can be deposed anywhere along the c-ring, e.g., in the middle of the c-ring, on one or both ends, or between the middle and one or both end. Further, the knobbed c-ring or o-ring can be utilized in conjunction with the connectors described in other figures, or any similar connector, instead of the c-ring 211 and anti-rotation pin 201 described previously.

In embodiments where the indentations or ridges do not substantially circumscribe the connector, the presence of the knob in the cavity or the gap between ridges has an advantage of limiting the rotation of the connector in the cavity or the gap between ridges, since the presence of the knob in the cavity or the gap between ridges limits any rotation to the width of the indention or the gap between ridges, unless additional force is applied in rotating the connector to force the knob(s) out of the indentation or the gap between ridges, as described in the following paragraph.

Figure 15A:
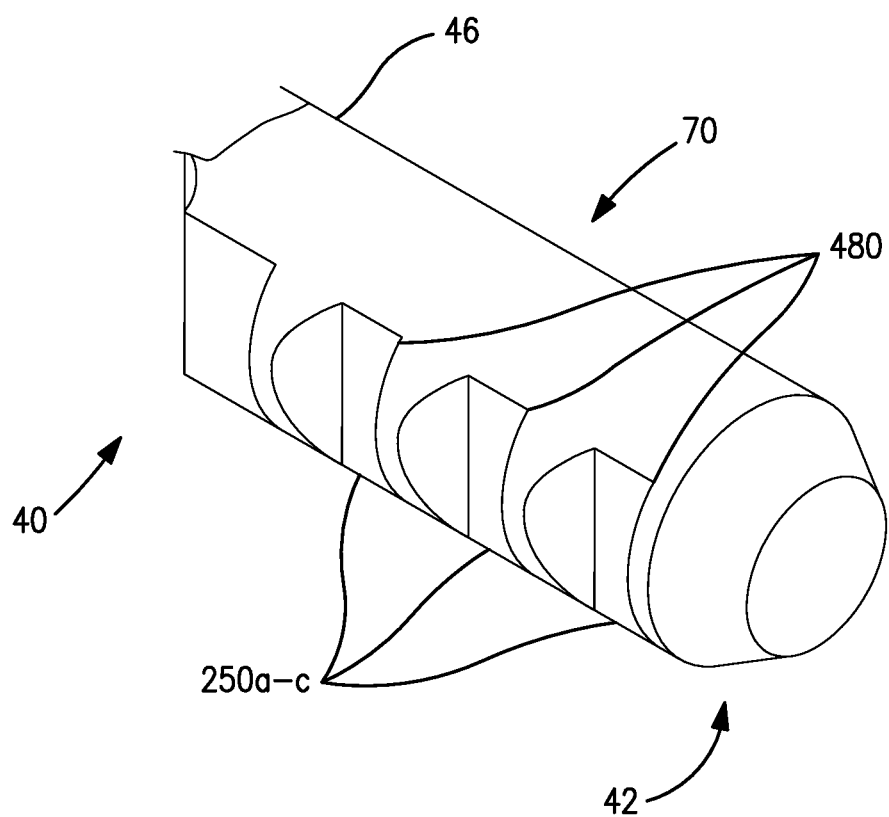
FIG. 15A is a perspective view of one embodiment of a connector of the bone joining device.
Figure 15B:
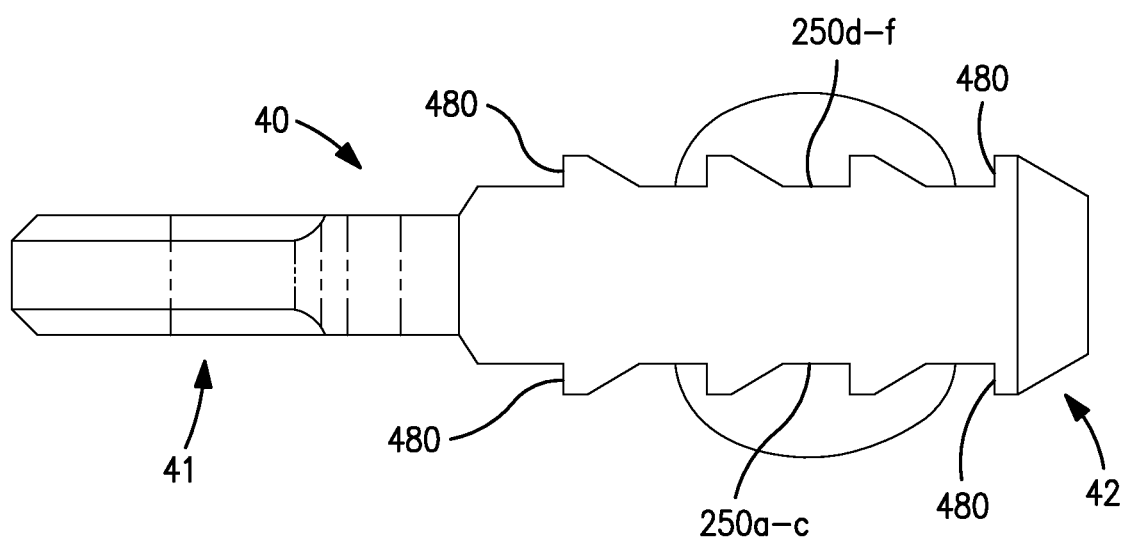
FIG. 15B is a cross-sectional view of one embodiment of a connector of the bone joining device.

The embodiment illustrated in FIGS. 15-16 has the advantage of being removable. For example, the connector 40 can be separated from the female component 20 by rotating the connector 40 in relation to the female component 20 (which can be achieved after implantation by rotating one bone piece in relation to the other). This causes the knobs 82, 84 to slide out of the indentation or the gap between ridges (e.g., 250a and 250d if fully implanted) and onto the portion of the shaft 70 between the opposing indentations or the gap between ridges (e.g., 250a and 250d). The connector 40 can then slide out of the female component 20 along that portion of the shaft 70.

As can be seen from the immediately preceding discussion, the presence of the knob in the indentation or the gap between ridges substantially limits the rotation of the connector in the cavity. However, rotating the connector in relation to the cavity is a means for disconnecting the male and female components of the device. As such, the shape and composition of the indentation or the gap between ridges, the c-ring or o-ring, and the knob(s) can be designed to have a balance between the ease with which the male and female components can be disconnected and the force required to overcome the ability of the knob in the cavity to prevent rotation of the connector in relation to the cavity. For example, coating the indentation or the gap between ridges with, e.g., silicone or Teflon to reduce the friction between the knob and the side of the indentation or the gap between ridges, or smoothing or angling the edge of the indentation or the gap between ridges where the knob encounters the wall of the indentation or the gap between ridges when the connector is rotated, makes separation of the male and female components easier and also makes it easier for the connector to be rotated to overcome the resistance to rotation caused by the presence of the knob in the indentation or the gap between ridges. Conversely, having a relatively long knob protruding into the indentation or the gap between ridges makes separation of the male and female components more difficult and also makes rotating the connector to overcome the resistance to rotation more difficult. The number and location(s) of the knob(s) also affect the ease with which rotating the connector to overcome the resistance to rotation can be achieved. For example, using a c-ring with only one knob (corresponding to only one set of axially deposed indentations or gaps between ridges) makes such rotation easier than using a c-ring with two knobs (corresponding to two sets of indentations or gaps between ridges). Also, deposing the knobs on the end of the c-ring makes overcoming the resistance to rotation easier than deposing the knobs toward the middle of the c-ring, since the c-ring requires greater bending distance and force when the knobs are deposed toward the middle in order for them to be pushed out of the cylindrical cavity. Additionally, the use of a c-ring made of a more flexible material makes overcoming the resistance to rotation easier then using a c-ring made of a less flexible material.

The devices described herein can be of any diameter appropriate for the particular bones being joined, as defined by the widest diameter of the spiraling thread 24, 34 of the female component 20 or the male component 30. In some embodiments, the diameter of either component is more than 5 mm. In other embodiments, the diameter of either component is about 5 mm, about 4 mm, about 3 mm, about 2 mm, about 1 mm, less than 1 mm, or any diameter in between, for example about 2.2 mm.

The bone fixation device can be fabricated from any appropriate material. In some embodiments, the device is not bioabsorbable, since it is anticipated that the device provides stability to the fusion site. Additionally, should the two bones joined by the device fail to fuse, the device would provide essential structural support to keep the two bones together. Non-limiting examples of materials that could be used to fabricate the device include (a) titanium, (b) an alloy of titanium with about 6% aluminum and about 4% vanadium, (c) nitinol, (d) stainless steel, and (e) a polymer such as poly ethyl ethyl ketone (PEEK).

This application is also directed to a method of joining a first bone piece with a second bone piece in a living vertebrate. The method comprises inserting the above-described bone fixation device between the first bone piece and the second bone piece such that the two bone pieces are securely joined.

The method can be used on any vertebrate species. In some embodiments, the vertebrate is a mammal, for example a human.

In some embodiments, the method comprises preparing the two bone pieces to provide a cut surface on each piece that will be joined to each other; inserting the first elongated stem portion longitudinally into the cut surface of the first bone piece such that the first end is inserted first and the first top is at, slightly below, or slightly above the cut surface of the first bone piece; inserting the second elongated stem portion longitudinally into the cut surface of the second bone piece such that the proximal end of the connector is at, slightly below, or slightly above the cut surface of the second bone piece; and inserting the connector into the opening in the first elongated stem portion.

In various embodiments, the connector is coupled to the second top at the proximal end by a coupling allowing the adjustable positioning of the connector in an angular direction in relation to the second top. In these embodiments, the method further comprises adjusting the position of the connector (e.g., by bending) in relation to the second top to form a preferred angle of flexion between the two bone pieces; and further inserting the connector into the first elongated stem portion.

In some embodiments, the position of the connector in relation to the second top can no longer be adjusted after the connector is further inserted into the first elongated stem portion.

These methods can be used to join or fuse any two bone pieces, for example two vertebrae or two halves of a broken bone. In some embodiments, the bone pieces are (a) two adjoining phalanges; (b) a phalanx and an adjoining metacarpal; (c) a phalanx and an adjoining metatarsal; or (d) bone pieces separated by a fracture or osteotomy of a bone diaphysis. Where the subject is a human, these bones can be in the hand or the foot.

In various embodiments, the bone pieces are in the foot of the mammal. The foot can have any condition for which the treatment involves a bone joining two bone pieces. Examples of such conditions include hammertoe, mallet toe, curly toe, or claw toe. In some embodiments, the interphalangeal, metatarsophalangeal or metacarpophalangeal joint is fused.

In other embodiments, the bone pieces are separated by an osteotomy that shortens the bone, for example a lesser metatarsal. An example of such a procedure that can utilize the instant method is a Weil osteotomy, which shortens a metatarsal to provide an improved metatarsal parabola. In those embodiments, the two bone pieces are from a single metatarsal bone that is subjected to an osteotomy of the diaphysis.

Using the illustrated embodiment, these methods can further comprise procedures wherein the first bone piece 50 and the second bone piece 50 are cut; the bone fixation device 10 is inserted between the first bone piece 50 and the second bone piece 50; the connector 40 is inserted into the cylindrical cavity 29. The connector 40 can be inserted until the cut surface on the first bone piece and the second bone piece are joined together.

In these methods, the device can further comprise marks on the first top 22 and on the second top 32, the marks aligning at the desired position of the male component 30 and female component 20 when the connector 40 is inserted into the first elongated stem portion (i.e., the female component) 20. In these embodiments, the first elongated stem portion 20 is inserted into the cut surface of the first bone piece 50 by screwing the first elongated stem portion 20 longitudinally into the cut surface of the first bone piece 50, and the second elongated stem portion 37 is inserted into the cut surface of the second bone piece 50 by screwing the second elongated stem portion 37 longitudinally into the cut surface of the second bone piece, where the mark on the first top 22 and on the second top 32 are adjacent to each other after insertion of the second elongated stem portion 37.

The various embodiments described above can be implanted using any appropriate tools known in the art. Alternative tools, particularly suited for the above embodiments, and methods of implanting the above bone fixation devices in a digit, exemplified on a lesser toe proximal and middle phalanges, are described below.

In some embodiments, to fuse the proximal and middle phalanges, the interphalangeal joint is exposed and the distal end of the proximal phalanx and the proximal end of the middle phalanx are cut off perpendicular to the long axis of each bone. This creates about a 3 mm gap between the bones. An optional pilot hole is then drilled, e.g., about 18 mm deep, in the proximal phalanx through the intramedullary canal.

Figure 17:
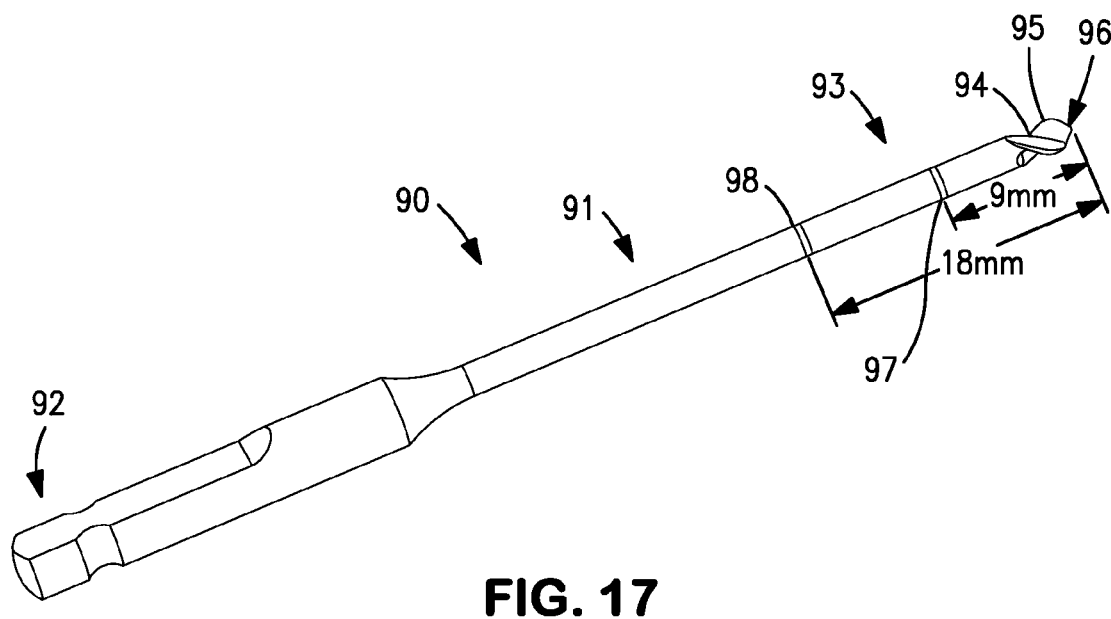
FIG. 17 is a perspective view of a pilot hole drilling device of one embodiment of the bone joining device.
Figure 22:
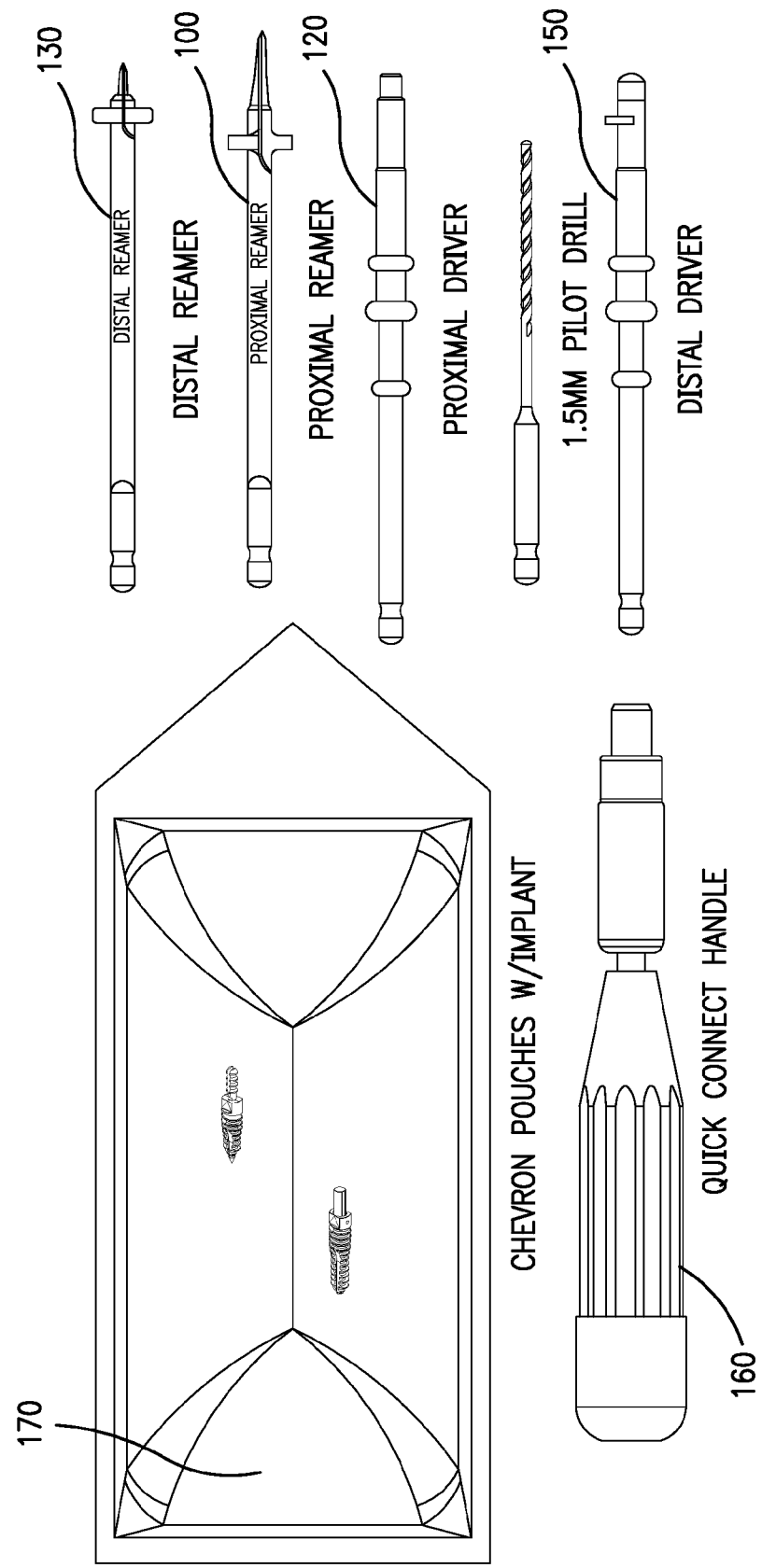
FIG. 22 is a perspective view of one embodiment of the bone joining device and tools used to install the device as prepared for packaging.

The pilot hole can be drilled using any appropriate pilot drill known in the art. In some embodiments, the pilot hole is drilled with a tool designed especially for the device described above, for example the pilot drill 90 shown in FIG. 17. Such a drill comprises an elongate shank 91 having a proximal end 92 and a distal end 93. The proximal end can comprise a handle or can be configured to join to a separate handle, for example, a quick connect handle 160 illustrated in FIG. 22. The distal end 93 terminates in a drill tip 94 comprising at least one spirally deposed flute 95 having a sharp outer edge and terminating in a point 96. In some embodiments, as in FIG. 17, there are two spirally deposed flutes 95. The cutting surface defined by the sharp outer edge has the same diameter as the shank 91. The diameter should be less than the diameter of the spiraling thread 24 of the female component 20, to be implanted therein. In some embodiments, the spiraling thread 24 of the female component 20 is 2.2 mm and the diameter of the shank 91 and spirally deposed flute 94 is 2.0 mm. Some embodiments of the pilot drill 90 further comprise a mark or marks (e.g., laser markings) indicating a distance from the point 96 to provide a guide for determining the depth of the hole to be drilled. For example, the pilot drill 90 illustrated in FIG. 17, has marks 97, 98 at 9 mm and 18 mm.

Figure 18:
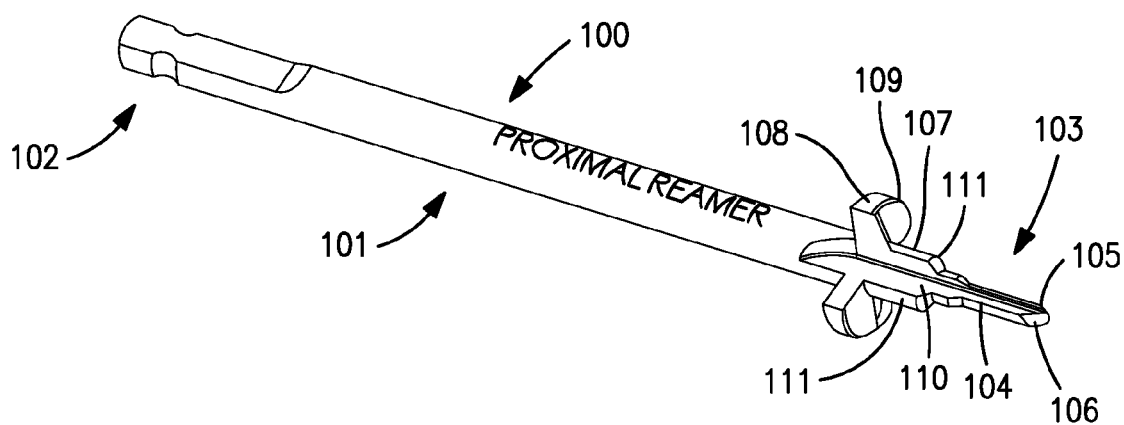
FIG. 18 is a perspective view of one embodiment of a proximal reamer.
Figure 19A:
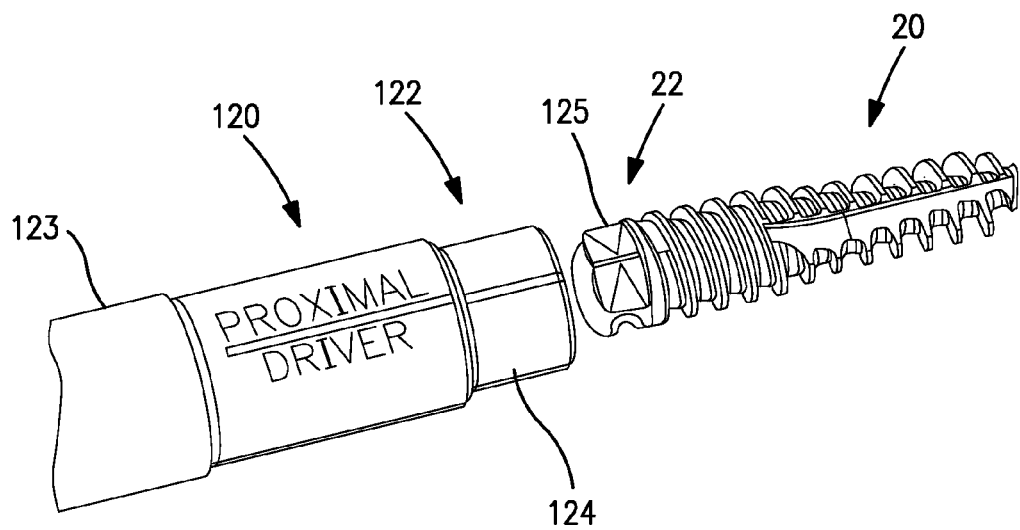
FIG. 19A is a perspective view of a portion of an embodiment of a proximal driver and a female component.
Figure 19B:
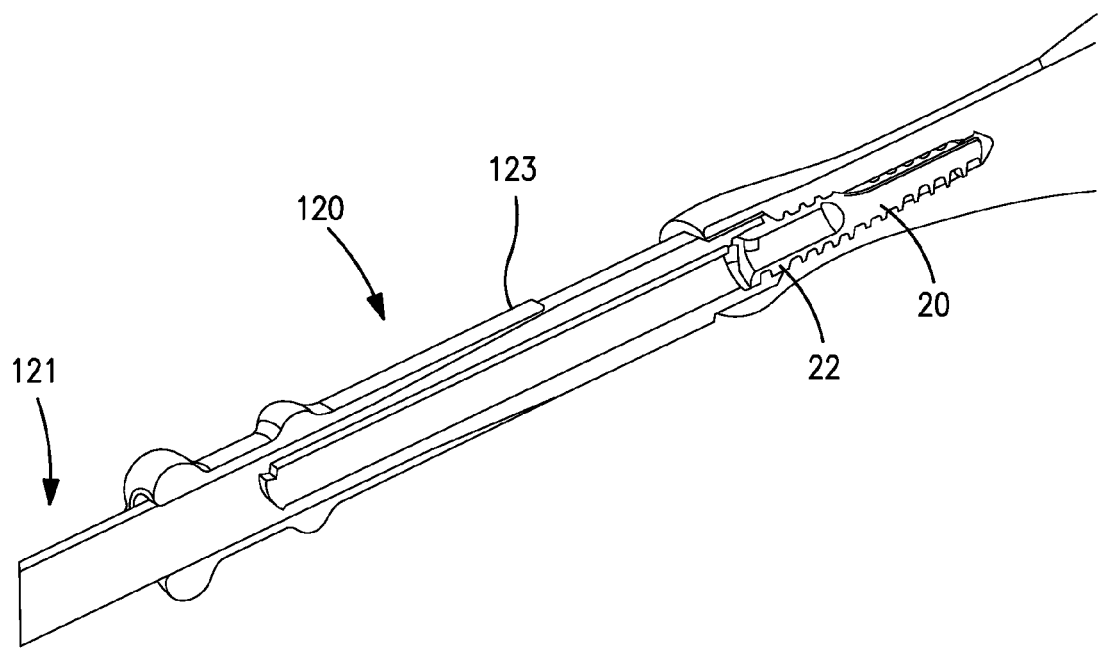
FIG. 19B is a perspective view of a section of an embodiment of the proximal driver and female component inserted into a bone.
Figure 20:
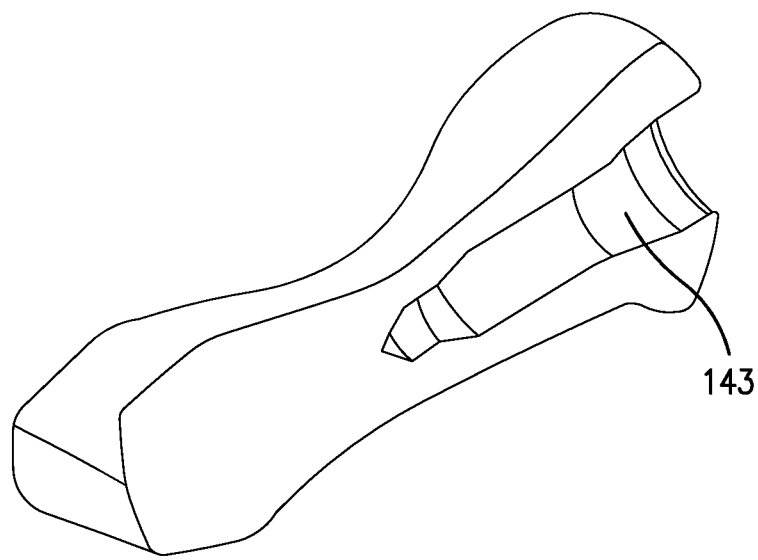
FIG. 20 is a perspective view of a sectioned bone showing a hole drilled by one embodiment of the distal reamer.
Figure 21:
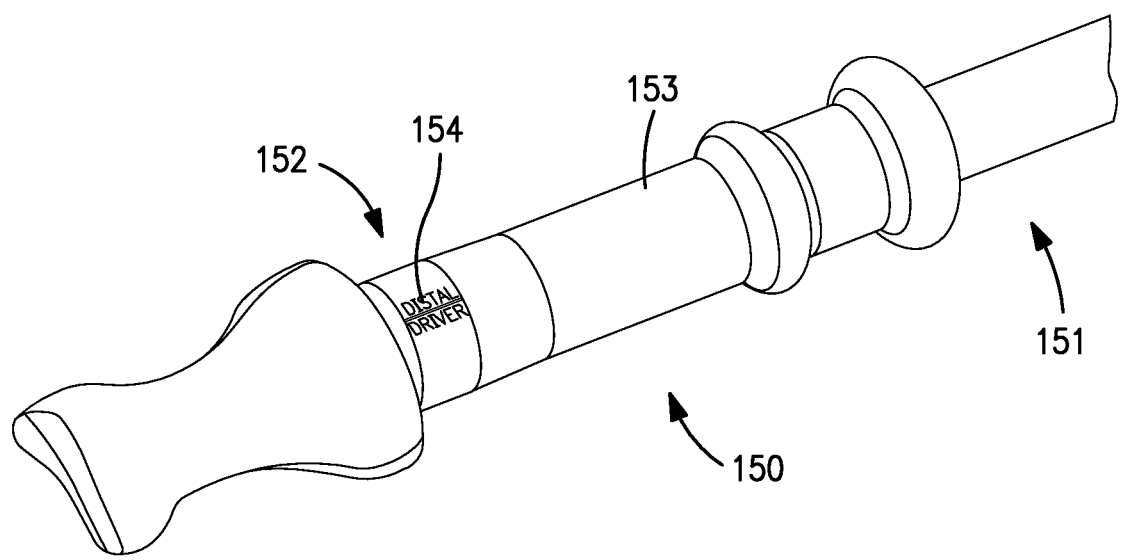
FIG. 21 is a perspective view of one embodiment of a distal driver aligned with a bone.

A 2.0 mm pilot hole can be drilled about 18 mm deep in the proximal phalanx through the intramedullary canal. This can be followed with a reamer to shape the hole to accommodate the female component 20. Alternatively, the reamer can form the hole in the absence of a pilot hole. In some embodiments, the reamer prepares a hole with a widened bore near the top to accommodate the top 22 of the female component, e.g., as illustrated in FIG. 18. A suitable reamer is illustrated in FIG. 18. The proximal reamer 100 comprises an elongate first shank 101 having a first proximal end 102 and a first distal end 103. The first proximal end can comprise a handle or can be configured to join to a separate handle, for example the quick connect handle 160. The first distal end 103 terminates in a first shaping drill end 104 terminating in a first point 106. Just proximal to the first point 106 is a plurality of first ridges 105 having sharp edges designed to cut the hole illustrated in FIG. 18. Proximal to the first ridges is a first short shaft 104, and proximal to the first short shaft 104 is a first shoulder 107, wider than the first short shaft 104 and having the approximate diameter of the first shank 101. Proximal to the first shoulder 107, is a first skirt 108, wider than the first shoulder and having a flat first distal surface 109. The proximal reamer 100 also comprises a first cutout 110, extending from the plurality of first ridges 105, through the first short shaft 104, the first shoulder 107, and the first skirt 108. The first cutout 110 has sharp lateral edges 111 designed to cut through the bone as the proximal reamer 100 is rotated and driven therein. In some embodiments, lateral edge 111 is continuous from along the first short shaft 104, through the first shoulder 107, and along the edge of the flat first distal surface 109, thus providing a sharp edge that can both cut a hole into the bone and face-off the bone face in an all-in-one operation. In some embodiments, an edge is present on the first distal surface 109 that provides for facing off the bone surface. In some embodiments, a plurality of edges is present on the first distal surface 109 that provides for facing off the bone surface.

The hole cut by the proximal reamer 100 preferably has a diameter smaller than the diameter of the spiraling thread 24 of the female component 20, such that when the female component 20 is screwed into the hole, the spiraling thread 24 will drive through the intramedullary canal of the phalanx. For example, in the alignment of the female component 20 with a suitable proximal reamer 100, the first ridges 105 and the first short shaft 104 can have a diameter of 2.0 mm, while the spiraling thread 24 of the female component 20 can have a diameter of 2.2 mm.

In some embodiments, the proximal reamer 100 reams a squared off surface 112 in the face of the bone, to allow the female component 20 to fit with the male component 30. The wide bore 113 cut by the first shoulder 107 allows the first top 22 to be "buried" in the bone.

Once the hole in the distal end of the proximal phalanx is prepared, e.g., by the proximal reamer 100, the female component 20 can be inserted. That insertion can be prepared using any suitable tool. A suitable tool for that purpose is the proximal driver 120. The proximal driver 120 comprises an elongate first shank 121 having a first proximal end 126 and a first distal end 122. The first proximal end can comprise a handle or can be configured to join to a separate handle, for example the quick connect handle 160. The first distal end 122 aids in the holding and guiding of the female component 20.

In some embodiments, the first distal end 122 of the proximal driver 120 comprises a first marking 124 (e.g., a laser marking) that aligns with a second marking 125 on the first top 22 of the female component 20 to easily align the proximal driver 120 with the female component 20.

In some embodiments, the proximal driver 120 comprises a second groove 127 in the first distal end 122. The second groove 127 can accommodate a retaining pin 128 in the first top 22 of the female component.

In some embodiments, the first shank 121 comprises a first slidable bobbin 123. The distal end 122 of the proximal driver 120 comprises two first half sections (not shown) operably linked to the first bobbin 123 such that sliding the first bobbin 123 forward forces these two first half sections together to hold the first top 22 of the female component 20 securely.

The first top 22 of the female component 20 is placed in the proximal driver 120 and the first bobbin 123 is slid forwards to securely hold the first top 22. The first top 22 is placed in the driver such that the first marking 124 on the proximal driver 120 lines up with the second marking 125 on the first top 22. The female component is then screwed into the proximal phalanx until the distal end 122 of the proximal driver 120 is even with or substantially even with the hole.

In some embodiments, the preparation of the proximal end of the middle phalanx and the insertion of the male component 30 therein proceeds similar to the insertion of the female component 20 into the distal end of the proximal phalanx described above.

After the proximal end of the middle phalanx is resected, an optional pilot hole is drilled about 9 mm deep into the intramedullary canal of the bone, using any suitable tool, for example the pilot drill 90. The hole for the male component 30 can then be prepared using any suitable tool, for example the distal reamer 130. That distal reamer 130 comprises an elongate second shank 131 having a second proximal end 132 and a second distal end 133. The second proximal end can comprise a handle or can be configured to join to a separate handle, for example the quick connect handle 160. The second distal end 133 comprises a second shaping drill end 134 terminating in a second point 136. Just proximal to the second point 136 is a plurality of second ridges 135 having sharp edges designed to cut a hole in the distal bone. Proximal to the ridges is a second short shaft 134, and proximal to the second short shaft 134 is a second shoulder 137, wider than the second short shaft 134 but having a smaller diameter than the second shank 131. Proximal to the second shoulder 137, is a second skirt 138, wider than the second shoulder and having a flat second distal surface 139. The distal reamer 130 also comprises a second cutout 140, extending from the plurality of second ridges 135, through the second short shaft 134, the second shoulder 137, and the second skirt 138. The second cutout 140 has sharp lateral edges 141 designed to cut through the bone as the distal reamer 130 is rotated and driven therein.

In an illustrated embodiment, the second short shaft 134, the second shoulder 137, and the second skirt 138 are shorter than the counterparts on the proximal reamer 100 because the male component 30, which is driven into the hole 143 made by the distal reamer 130, is shorter than the female component 40, which is driven into the hole made by the proximal reamer 100.

The hole 143 cut by the distal reamer 130 preferably has a diameter smaller than the diameter of the spiraling thread 34 of the male component 30, such that when the male component 30 is screwed into the hole, the spiraling thread 34 will drive through the intramedullary canal of the phalanx. For example, the second ridges 135 and the second short shaft 134 have a diameter of 2.0 mm, while the spiraling thread 34 of the male component 30 has a diameter of 2.2 mm. The distal reamer 130 also reams a flat surface 144 in the face of the bone 50.

Once the hole in the proximal end of the middle phalanx is prepared, e.g., by the distal reamer 130, the male component 30 can be inserted. That insertion can be prepared using any suitable tool. A suitable tool for that purpose is the distal driver 150. The distal driver 150 comprises an elongate second shank 151 having a second proximal end 156 and a second distal end 152. The second proximal end can comprise a handle or can be configured to join to a separate handle, for example, the quick connect handle 160 illustrated in FIG. 22.

In some embodiments, the second distal end 152 of the distal driver 150 comprises a third marking 154 (e.g., a laser marking) that aligns with a fourth marking 155 on the first top 32 of the male component 30 to easily align the distal driver 150 with the male component 30.

In some embodiments, the second shank 151 comprises a second slidable bobbin 153. In some embodiments, the second distal end 152 of the distal driver 150 comprises two second half sections (not shown) operably linked to the second bobbin 153 such that sliding the second bobbin 153 forward forces these two second half sections together to hold the second top 32 of the male component 30 securely.

The first top 32 of the male component 30 is placed in the distal driver 150 and the second bobbin 153 is slid forward to securely hold the first top 32. The first top 32 is placed in the distal driver 150 such that the third marking 154 on the distal driver 150 lines up with the fourth marking 155 on the first top 32. The male component 30 is then screwed into the middle phalanx.

The connector 40 can be adjusted to the desired angle in relation to the second top 32 at this point by, for example, bending the connector 40 to desired angle using leverage from the distal driver 150. Alternatively, the connector 40 can be partially pushed into the female component 20 before the angle is adjusted. Where the surgeon decides not to change the angle of the connector 40, the connector 40 can be fully inserted into the female component 20. Changing the angle of the connector 40 may result in partial insertion of connector 40 into the female component 20, depending on the degree and location of the bend.

After insertion of the device, the two bones 50 are aligned as depicted in FIG. 8.

As discussed above, the proximal reamer 100, the proximal driver 120, the distal reamer 130 and the distal driver 150 can each have their own handle or can utilize a common handle, for example the quick connect handle 160. Connecting means for such handles are known in the art. In some embodiments, the elongate shank of any of these tools can comprise gripping elements, e.g., a rubber grip, to allow the surgeon to use the tool without a handle while maintaining a firm grip on the tool. In some embodiments, any of the proximal or distal reamer or proximal or distal driver can comprise, on its proximal end the cutting portion of a proximal or distal reamer or proximal or distal driver. For example, the proximal reamer (comprising a shaping drill end with a flat first distal surface 109 at its distal end) can comprise the shaping drill end of the distal reamer (comprising a shaping drill end with a flat second distal surface 139) at is proximal end. Alternatively, the proximal reamer can comprise at its proximal end the slidable bobbin 123 and the two first half sections operably linked to the bobbin of the proximal driver. Any combination tool independently having, at its proximal and distal ends, any of the shaping drill end of the proximal or distal reamer or the bobbin and two half sections of the proximal or distal driver is envisioned herewith. Thus, multiple tools may be combined into a single tool, e.g., with one end for reaming and the other end for driving. The portion of the handle between the two tools may have grooves, cross hatching, or a gripping material to provide gripping capabilities for the person using the tools.

The each, any or all of the various tools described herein can also be provided sterilized in a package, such as a molded sterilization tray. Additionally, the bone fixation device 10, in any embodiment described above, can be packaged in a sterile package as appropriate, for example in a chevron pouch 170.

Additionally, the various bone joining devices described above may include templates for use when drilling, reaming, driving, inserting the device or cutting the bones. The templates are useful to ensure that the installation of the device is accomplished with precision and accuracy. For example, a template may be used to align the proximal reamer or distal reamer to the bone, such that the hole prepared by the reamer is parallel with the long axis of the bone. Such a template could comprise a component that attaches (e.g., by screws) to the end of the bone and extends outward from the bone and provide a hole to provide a straight guide for the cutting tip of the reamer. The design and preparation of such templates are known in the art.

Definitions and methods described herein are provided to better define the present invention and to guide those of ordinary skill in the art in the practice of the present invention. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

What is claimed is:

1. A device for joining bone, comprising:
   a first component, comprising:
      a first elongated stem portion, comprising:
         a first end;
         a first top opposite the first end; and
         an opening extending axially from the first top toward the first end comprising an open end, a closed end opposite the open end, a wall extending from the open end to the closed end, and at least one recess circumscribing the wall; and
   a second component, comprising:
      a second elongated stem portion, comprising:
         a second end; and
         a second top opposite the first end; and
      a connector portion extending from the second top, the connector portion comprising:
         an elongated shaft;
         a first connector end;
         a top of the elongated shaft near the first connector end;
         a second connector end opposite the first connector end,
         at least one ring proximate to the second connector end;
         at least one slit extending along a length of the connector from the second connector end toward the top of the connector portion; and
         at least one groove along the length of the connector,
      wherein the connector portion is configured to couple to the second elongated stem portion, and the connector portion is capable of insertion into the opening in the first elongated stem portion and configured to lock the connector portion and the first component.

2. The device of claim 1, wherein the first elongated stem portion further comprises:
   at least one pin hole extending from an exterior surface of the first elongated stem portion into the opening; and
   at least one pin configured to engage the pin hole of the first elongated stem portion and the at least one groove of the connector portion.

3. The device of claim 2, wherein the first elongated stem portion further comprises at least one indentation circumscribing at least a portion of the first top and engaging the at least one pin hole.

4. The device of claim 1, wherein the connector portion further comprises at least two shaft rings.

5. The device of claim 4, wherein a first shaft ring of the at least two shaft rings is positioned on a first side of the at least one groove and a second shaft ring of the at least two shaft rings is positioned on a second side of the at least one groove.

6. The device of claim 1, further comprising:
   a c-ring with at least one knob extending inward;
   at least one indentation circumscribing at least a portion of the first top of the first elongated stem portion;
   at least one hole extending from an exterior surface of the first elongated stem portion into the opening; and
   wherein the c-ring is configured to be positioned in the at least one indentation with the at least one knob inserted into the at least one hole.

7. The device of claim 1, wherein the top of the elongated shaft of the connector portion is configured to fit into the opening in the first elongated stem portion of the first component.

8. The device of claim 1, wherein
   the first elongated stem portion is configured for insertion from the first end longitudinally into an opening in a first bone piece, and
   the second elongated stem portion is configured for insertion from the second end longitudinally into an opening in a second bone piece.

9. The device of claim 1, further comprising:
   a first mark on the first top of the first component; and
   a second mark on the second top of the connector portion, the marks aligning at the desired position of the first component and second component when the connector portion of the second component is inserted into the opening of the first component.

10. A method of joining or fusing a first bone piece with a second bone piece, the method comprising:
    inserting the bone joining device of claim 1 between the first bone piece and the second bone piece.

11. The device of claim 1, wherein the connector portion is capable of unlocking from the first elongated stem portion and being removed from therein.

12. The device of claim 11, wherein the connector portion is configured to unlock from the first elongated stem portion by rotating the connector portion.

13. The device of claim 1, wherein the first component is a female component and the second component is a male component.

14. The device of claim 1, wherein the first component further comprises an anchoring means on an exterior surface of the first component.

15. The device of claim 1, wherein the first component further comprises at least one retaining pin or recess near the first top of the first elongated stem portion.

16. The device of claim 15, wherein the at least one retaining pin is configured to engage at least one of the connector portion and a tool.

17. The device of claim 1, wherein the second component further comprises an anchoring means on an exterior surface of the second component.

18. The device of claim 1, wherein the at least one ring comprises an edge on a side of the connector portion near the second top of the second elongated stem portion.

19. The device of claim 1, wherein the at least one ring is configured to engage the at least one recess in the opening of the first elongated stem portion.

20. A driver tool for screwing the device of claim 9 into an intramedullary canal of a bone, the driver tool comprising:
an elongate shank having a proximal end and a distal end;
wherein the distal end comprises a third mark that aligns with the first mark of the first component or the second mark of the second component of the device of claim 9, and the distal end is configured to engage the first component or the second component.

21. The driver tool of claim 20 further comprising:
a groove in the distal end of the driver tool, the groove configured to engage one or more retaining pins of the first component of the device of claim when the distal end engages the first component.

22. The driver tool of claim 20, further comprising:
a handle configured to attach at the proximal end of the elongated shank.

23. A kit comprising:
a device comprising:
a first component, comprising:
a first elongated stem portion, comprising:
a first end;
a first top opposite the first end; and
an opening extending axially from the first top toward the first end; and
a second component, comprising:
a second elongated stem portion, comprising:
a second end; and
a second top opposite the first end; and
a connector portion extending from the second top, the connector portion comprising:
an elongated shaft;
a first connector end;
a top of the elongated shaft near the first connector end; and
a second connector end opposite the first connector end,
wherein the connector portion is configured to couple to the second elongated stem portion, and the connector portion is capable of insertion into the opening in the first elongated stem portion and configured to lock the connector portion and the first component;
at least one reamer tool comprising:
an elongate shank having a first end and a second end; and
a first shaping drill end near the second end and terminating in a first point, the first shaping drill end, further comprising:
a plurality of first ridges having sharp edges immediately proximal to the first point;
a first short shaft immediately proximal to the first ridges;
a first shoulder wider than the first short shaft and immediately proximal to the first short shaft;
a first skirt with a first distal surface, wider than the first shoulder and immediately proximal to the first shoulder; and
a first cutout extending from the plurality of first ridges through the first short shaft, the first shoulder, and the first skirt; and
at least one driver tool for screwing the device into an intramedullary canal of a bone, the driver tool comprising:
an elongate shank having a proximal end and a distal end,
wherein the distal end comprises a third mark that aligns with the first mark of the first component or the second mark of the second component of the device, and the distal end is configured to engage the first component or the second component, and
wherein the device, the at least one reamer tool, and the at least one driver tool are sterile.

24. The kit of claim 23, wherein the first shoulder of the reamer tool comprises a flat first distal surface.

25. The kit of claim 23, wherein the reamer tool further comprises a handle coupled to the first end of the elongated first shank.

26. The kit of claim 23, further comprising:
a handle configured to join the at least one reamer tool or the at least one driver tool to the device, wherein the handle is sterile.

27. The kit of claim 23, wherein the first cutout of the reamer tool has lateral edges.

28. A method of joining or fusing a first bone piece with a second bone piece, the method comprising:
inserting a bone joining device between the first bone piece and the second bone piece, the bone joining device comprising:
a first component, comprising:
a first elongated stem portion, comprising:
a first end;
a first top opposite the first end; and
an opening extending axially from the first top toward the first end; and
a second component, comprising:
a second elongated stem portion, comprising:
a second end; and
a second top opposite the first end; and
a connector portion extending from the second top, the connector portion comprising:
an elongated shaft;
a first connector end;
a top of the elongated shaft near the first connector end; and
a second connector end opposite the first connector end,
wherein the connector portion is configured to couple to the second elongated stem portion, and the connector portion is capable of insertion into the opening in the first elongated stem portion and configured to lock the connector portion and the first component;

reaming a first hole into the first bone piece and a second hole into the second bone piece;

inserting the first elongated stem portion of the first component longitudinally into the first hole of the first bone piece such that the first end is inserted first and the first top is aligned proximate to a cut surface of the first bone piece;

inserting the second elongated stem portion of the second component longitudinally into the second hole of the second bone piece such that the proximal end of the connector portion is aligned proximate to a cut surface of the second bone piece; and inserting the connector portion of the second component into the opening in the first elongated stem portion of the first component.

29. The method of claim 28, wherein:

the first bone piece is faced and reamed with a reamer tool comprising:
  an elongate shank having a first end and a second end; and
  a first shaping drill end near the second end and terminating in a first point, the first shaping drill end, further comprising:
    a plurality of first ridges having sharp edges immediately proximal to the first point;
    a first short shaft immediately proximal to the first ridges;
    a first shoulder wider than the first short shaft and immediately proximal to the first short shaft;
    a first skirt with a first distal surface, wider than the first shoulder and immediately proximal to the first shoulder; and
    a first cutout extending from the plurality of first ridges through the first short shaft, the first shoulder, and the first skirt; and
the second bone piece is faced and reamed with the reamer tool of claim 20.

30. The method of claim 28, wherein:

the first elongated stem portion of the first component is inserted longitudinally into the cut surface of the first bone piece with a driver tool comprising:
  an elongate shank having a proximal end and a distal end,
  wherein the distal end comprises a third mark that aligns with a first mark of the first component or a second mark of the second component of the device, and the distal end is configured to engage the first component or the second component; or
the second elongated stem portion of the second component is inserted longitudinally into the cut surface of the second bone piece with the driver tool.

31. The method of claim 28, further comprising:

adjusting the position of the connector portion in relation to the second top of the second component to form a preferred angle of flexion between the two bone pieces.

32. The method of claim 31, wherein:

the connector portion of the second component is bent to the preferred angle of flexion between the first and second bone pieces before insertion of the connector portion into the opening of the first elongated stem portion of the first component; or the connector portion of the second component is bent to the preferred angle of flexion between the first and second bone pieces after partial insertion of the connector portion into the opening of the first elongated stem portion of the first component.

33. The method of claim 31, wherein the connector portion of the second component is bent to the preferred angle of flexion between the two bone pieces with a driver tool comprising an elongate shank having a proximal end and a distal end, wherein the distal end comprises a third mark that aligns with a first mark of the first component or a second mark of the second component of the device, and the distal end is configured to engage the first component or the second component.

34. The method of claim 28, wherein inserting the connector portion of the second component into the opening in the first elongated stem portion of the first component comprises aligning a first mark on the first component and a second mark on the second component.

* * * * *

UNITED STATES PATENT AND TRADEMARK OFFICE
CERTIFICATE OF CORRECTION

PATENT NO. : 9,072,562 B2  Page 1 of 1
APPLICATION NO. : 13/646146
DATED : July 7, 2015
INVENTOR(S) : Weiner et al.

It is certified that error appears in the above-identified patent and that said Letters Patent is hereby corrected as shown below:

In the claims

Column 25, Line 41: Claim 29, Delete "of claim 20"

Signed and Sealed this
First Day of December, 2015

Michelle K. Lee
*Director of the United States Patent and Trademark Office*